US010487148B2

(12) United States Patent
Wyss-Coray et al.

(10) Patent No.: US 10,487,148 B2
(45) Date of Patent: Nov. 26, 2019

(54) METHODS AND COMPOSITIONS FOR TREATING AGING-ASSOCIATED IMPAIRMENTS

(71) Applicants: THE BOARD OF TRUSTEES OF THE LELAND STANFORD JUNIOR UNIVERSITY, Stanford, CA (US); U.S. GOVERNMENT AS REPRESENTED BY THE DEPARTMENT OF VETERNS AFFAIRS, Washington, DC (US); THE REGENTS OF THE UNIVERSITY OF CALIFORNIA, Oakland, CA (US); ALKAHEST, INC., San Carlos, CA (US)

(72) Inventors: Anton Wyss-Coray, Palo Alto, CA (US); Saul A. Villeda, Lancaster, CA (US); Karoly Nikolich, Redwood City, CA (US)

(73) Assignees: THE BOARD OF TRUSTEES OF THE LELAND STANFORD JUNIOR UNIVERSITY, Stanford, CA (US); U.S. GOVERNMENT AS REPRESENTED BY THE DEPARTMENT OF VETERANS AFFAIRS, Washington, DC (US); THE REGENTS OF THE UNIVERSITY OF CALIFORNIA, Oakland, CA (US); ALKAHEST, INC., San Carlos, CA (US)

( * ) Notice: Subject to any disclaimer, the term of this patent is extended or adjusted under 35 U.S.C. 154(b) by 0 days.

(21) Appl. No.: 15/574,795

(22) PCT Filed: May 17, 2016

(86) PCT No.: PCT/US2016/032907
§ 371 (c)(1),
(2) Date: Nov. 16, 2017

(87) PCT Pub. No.: WO2016/187217
PCT Pub. Date: Nov. 24, 2016

(65) Prior Publication Data
US 2018/0298102 A1   Oct. 18, 2018

Related U.S. Application Data

(63) Continuation-in-part of application No. 14/280,939, filed on May 19, 2014, which is a continuation of application No. 13/575,437, filed as application No. PCT/US2011/022916 on Jan. 28, 2011, now abandoned.

(60) Provisional application No. 61/298,998, filed on Jan. 28, 2010, provisional application No. 62/163,222, filed on May 18, 2015.

(51) Int. Cl.
| A61M 1/36 | (2006.01) |
| A61P 25/28 | (2006.01) |
| C07K 16/28 | (2006.01) |
| C12N 15/113 | (2010.01) |
| A61K 31/7088 | (2006.01) |

(52) U.S. Cl.
CPC ...... *C07K 16/2833* (2013.01); *A61K 31/7088* (2013.01); *A61M 1/3621* (2013.01); *A61P 25/28* (2018.01); *C12N 15/1138* (2013.01); *A61M 2202/07* (2013.01); *C12N 2310/11* (2013.01); *C12N 2310/341* (2013.01)

(58) Field of Classification Search
CPC ........ C07K 16/28; C12N 15/113; A61M 1/36; A61P 25/28; A61K 31/7088
See application file for complete search history.

(56) References Cited

U.S. PATENT DOCUMENTS

| 4,872,983 | A | 10/1989 | Diamantoglou et al. |
| 5,240,614 | A | 8/1993 | Ofsthun et al. |
| 5,916,202 | A | 6/1999 | Haswell |
| 6,416,487 | B1 | 7/2002 | Braverman et al. |
| 6,419,830 | B2 | 7/2002 | Strom et al. |
| 6,423,024 | B1 | 7/2002 | Strom et al. |
| 6,632,174 | B1 | 10/2003 | Breznitz |
| 6,855,121 | B1 | 2/2005 | Chan et al. |
| 6,946,546 | B2 | 9/2005 | Vaughan et al. |
| 7,196,162 | B2 | 3/2007 | Quirk et al. |

(Continued)

FOREIGN PATENT DOCUMENTS

| EP | 0184040 B1 | 4/1993 |
| EP | 2341138 A1 | 7/2011 |

(Continued)

OTHER PUBLICATIONS

Ameer et al., Kidney International, 59:1544-1550, published online Oct. 25, 2000 (Year: 2000).*

(Continued)

*Primary Examiner* — Kimberly Ballard
*Assistant Examiner* — Stacey N MacFarlane
(74) *Attorney, Agent, or Firm* — Casimir Jones, S.C.; Tanya A. Arenson

(57) ABSTRACT

Methods of treating an adult mammal for an aging-associated impairment are provided. Aspects of the methods include reducing the 2-microglobulin (B2M) level in the mammal in a manner sufficient to treat the mammal for the aging-associated impairment. A variety of aging-associated impairments may be treated by practice of the methods, which impairments include cognitive impairments.

5 Claims, 13 Drawing Sheets
Specification includes a Sequence Listing.

(56) References Cited

U.S. PATENT DOCUMENTS

| | | | |
|---|---|---|---|
| 7,608,406 | B2 | 10/2009 | Valkirs et al. |
| 7,739,056 | B2 | 6/2010 | Landfield et al. |
| 7,785,601 | B2 | 8/2010 | Schaebitz et al. |
| 7,851,172 | B2 | 12/2010 | Lovell et al. |
| 7,908,090 | B2 | 3/2011 | Kim et al. |
| 8,211,310 | B2 | 7/2012 | Young et al. |
| 8,257,922 | B2 | 9/2012 | Liew et al. |
| 8,272,518 | B2 | 9/2012 | Fujita et al. |
| 8,349,550 | B2 | 1/2013 | Brady et al. |
| 8,772,042 | B2 | 7/2014 | Yalkinoglu et al. |
| 8,828,977 | B2 | 9/2014 | Zahos et al. |
| 9,161,968 | B2 | 10/2015 | Wyss-Coray et al. |
| 9,511,094 | B2 | 12/2016 | Fraser et al. |
| 9,770,486 | B2 | 9/2017 | Wyss-Coray et al. |
| 9,782,457 | B2 | 10/2017 | Chandler et al. |
| 2002/0055158 | A1 | 5/2002 | Greene et al. |
| 2002/0143283 | A1 | 10/2002 | Braverman et al. |
| 2002/0151064 | A1 | 10/2002 | Rothenberg et al. |
| 2003/0139332 | A1 | 7/2003 | Noble et al. |
| 2003/0157687 | A1 | 8/2003 | Greene et al. |
| 2004/0120937 | A1 | 6/2004 | Wilson |
| 2004/0127445 | A1 | 7/2004 | Liew et al. |
| 2004/0141946 | A1 | 7/2004 | Schaebitz et al. |
| 2004/0254152 | A1 | 12/2004 | Monje et al. |
| 2005/0221348 | A1 | 10/2005 | Ray et al. |
| 2005/0244448 | A1 | 11/2005 | Chen et al. |
| 2006/0094064 | A1 | 5/2006 | Ray et al. |
| 2006/0198851 | A1 | 9/2006 | Basi et al. |
| 2006/0263759 | A1 | 11/2006 | Alves-Filho et al. |
| 2007/0037200 | A1 | 2/2007 | Ray et al. |
| 2007/0155725 | A1 | 7/2007 | Li et al. |
| 2007/0190055 | A1 | 8/2007 | Ambati |
| 2008/0026485 | A1 | 1/2008 | Hueber et al. |
| 2008/0057590 | A1 | 3/2008 | Urdea et al. |
| 2008/0125354 | A1 | 5/2008 | Fields et al. |
| 2009/0143394 | A1 | 6/2009 | Wyss-Coray et al. |
| 2009/0181008 | A1 | 7/2009 | Ray et al. |
| 2009/0209615 | A1 | 8/2009 | Lipton et al. |
| 2009/0239241 | A1 | 9/2009 | Ray et al. |
| 2010/0080850 | A1 | 4/2010 | Hubbel et al. |
| 2010/0119496 | A1 | 5/2010 | Wilkison et al. |
| 2010/0124756 | A1 | 5/2010 | Ray et al. |
| 2010/0258496 | A1 | 10/2010 | Hidaka et al. |
| 2010/0310609 | A1 | 12/2010 | Watson et al. |
| 2010/0324079 | A1 | 12/2010 | Ohyagi |
| 2011/0117100 | A1 | 5/2011 | Britschgi et al. |
| 2011/0142848 | A1 | 6/2011 | Chung et al. |
| 2011/0202284 | A1 | 8/2011 | McReynolds et al. |
| 2011/0212854 | A1 | 9/2011 | Ray et al. |
| 2011/0243947 | A1 | 10/2011 | Doody et al. |
| 2012/0095000 | A1 | 4/2012 | Wyss-Coray et al. |
| 2012/0230941 | A1 | 9/2012 | Sing et al. |
| 2013/0040844 | A1 | 2/2013 | Wyss-Coray et al. |
| 2013/0302322 | A1 | 11/2013 | Wong et al. |
| 2014/0011689 | A1 | 1/2014 | Sandip et al. |
| 2014/0121438 | A1 | 5/2014 | Long et al. |
| 2014/0255424 | A1 | 9/2014 | Wyss-Coray et al. |
| 2014/0294724 | A1 | 10/2014 | Chain et al. |
| 2015/0031562 | A1 | 1/2015 | Kantor et al. |
| 2015/0079045 | A1 | 3/2015 | Kong |
| 2015/0157664 | A1 | 6/2015 | Wyss-Coray et al. |
| 2016/0208011 | A1 | 7/2016 | Wyss-Coray et al. |
| 2017/0081415 | A1 | 3/2017 | Wong et al. |
| 2017/0232118 | A1 | 8/2017 | Wyss-Coray et al. |

FOREIGN PATENT DOCUMENTS

| | | |
|---|---|---|
| RU | 2428997 C1 | 9/2011 |
| RU | 2470677 C1 | 12/2012 |
| UA | 35656 C2 | 4/2001 |
| WO | WO 1990011287 | 10/1990 |
| WO | WO 1997038314 | 10/1997 |
| WO | WO 1999006098 | 2/1999 |
| WO | WO 2002006480 A2 | 1/2002 |
| WO | WO 2003006006 | 1/2003 |
| WO | WO 2003020403 | 3/2003 |
| WO | WO 2004019043 | 3/2004 |
| WO | WO 2004060425 | 7/2004 |
| WO | WO 2005052592 A2 | 6/2005 |
| WO | WO 2005106492 A2 | 11/2005 |
| WO | WO 2006102170 A2 | 9/2006 |
| WO | WO 2006133423 A1 | 12/2006 |
| WO | WO 2007059135 A2 | 5/2007 |
| WO | WO 2008014314 | 1/2008 |
| WO | WO 2008146018 | 12/2008 |
| WO | WO 2009023814 A2 | 2/2009 |
| WO | WO 2009055729 A1 | 4/2009 |
| WO | WO 2010017443 | 2/2010 |
| WO | WO 2010041617 | 4/2010 |
| WO | WO 2011094535 A2 | 8/2011 |
| WO | WO 2013142135 A1 | 9/2013 |
| WO | WO 2015081166 A1 | 6/2015 |
| WO | WO 2015088915 A1 | 6/2015 |
| WO | WO 2015161112 A1 | 10/2015 |
| WO | WO 2016187217 A2 | 11/2016 |
| WO | WO 2016205004 A2 | 12/2016 |
| WO | WO 2017120461 A1 | 7/2017 |

OTHER PUBLICATIONS

Smith et al, Nature Medicine, 21(8): 932-39, published online Jul. 6, 2015 (Year: 2015).*

Adachi et al., "Intravascular lymphomatosis: a case report" No Shinkei Geka. Jul. 2001;29(7):659-65. Original in Japanese (English abstract obtained from pubmed).

Adair et al., "Measurement of gelatinase B (MMP-9) in the cerebrospinal fluid of patients with vascular dementia and Alzheimer disease." Stroke. Jun. 2004;35(6):e159-62.

Adkins et al. "Toward a human blood serum proteome: analysis by multidimensional separation coupled with mass spectrometry." Mol Cell Proteomics. Dec. 2002;1(12):947-55.

Anderson et al., "High resolution two-dimensional electrophoresis of human plasma proteins." Proc Natl Acad Sci U S A. Dec. 1977;74(12):5421-5.

Anderson et al., "The human plasma proteome: history, character, and diagnostic prospects." Mol Cell Proteomics. Nov. 2002;1(11):845-67.

Baba et al., "Timp-3 deficiency impairs cognitive function in mice." Lab Invest. Dec. 2009;89(12):1340-7.

Berezovskaya et al., "Colony stimulating factor-1 potentiates neuronal survival in cerebral cortex ischemic lesion." Acta Neuropathol. Nov. 1996;92(5):479-86.

Bhattacharya "Placental umbilical cord whole blood transfusion: a safe and genuine blood substitute for patients of the under-resourced world at emergency." J Am Coll Surg. 2005. Submitted 34 pages.

Bhattacharya "Study of the utility of placental cord blood in meeting the transfusion needs of beta-thalassaemic patients" Regional Health Forum, 2008. pp. 16-27.

Boissonneault et al., "Powerful beneficial effects of macrophage colony-stimulating factor on beta-amyloid deposition and cognitive impairment in Alzheimer's disease." Brain. Apr. 2009;132(Pt 4):1078-92.

Borlongan et al., "Central nervous system entry of peripherally injected umbilical cord blood cells is not required for neuroprotection in stroke." Stroke. Oct. 2004;35(10):2385-9.

Bouchard et al. "Aging and brain rejuvenation as systemic events", J. Neurochem. Jan. 2015; 132(1):5-19.

Brew et al., "The tissue inhibitors of metalloproteinases: An ancient family with structural and functional diversity," Biochimica et Biophysica Acta (2010) 1803: 55-71).

Britschgi et al., "Blood protein signature for the early diagnosis of Alzheimer disease." Arch Neurol. Feb. 2009;66(2):161-5.

Cheung et al., "Serum β-2 microglobulin predicts mortality in people with diabetes." Eur J Endocrinol. May 17, 2013;169(1):1-7.

Conboy et al., "Heterochronic parabiosis for the study of the effects of aging on stem cells and their niches." Cell Cycle. Jun. 15, 2012;11(12):2260-7.

(56) References Cited

OTHER PUBLICATIONS

Conboy et al., "Heterochronic parabiosis: historical perspective and methodological considerations for studies of aging and longevity." Aging Cell. Jun. 2013;12(3):525-30.

Conboy et al., "Rejuvenation of aged progenitor cells by exposure to a young systemic environment." Nature. Feb. 17, 2005;433(7027):760-4.

Fedoroff e al., "Role of colony stimulating factor-1 in brain damage caused by ischemia." Neurosci Biobehav Rev. Mar. 1997;21(2):187-91.

Gomez, et al., "Tissue inhibitors of metalloproteinases: structure, regulation and biological functions," European Journal of Cell Biology (1997) 74: 111-22).

Gowing et al., "Macrophage colony stimulating factor (M-CSF) exacerbates ALS disease in a mouse model through altered responses of microglia expressing mutant superoxide dismutase." Exp Neurol. Dec. 2009;220(2):267-75.

Jha, Alok. "Young blood can reverse some effects of ageing, study finds", The Guardian, Oct. 17, 2012, 4 pages.

Kassiri, et al., "Tissue inhibitor of metalloproteinases (TIMPs) in heart failure," Heart Failure Reviews (2012) 17: 693-706).

Katcher "Studies that shed new light on aging." Biochemistry (Mosc). Sep. 2013;78(9):1061-70.

Komosinkska-Vassev, et al., "Age-and gender-dependent changes in connective tissue remodeling: physiological differences in circulating MMP-3, MMP-10, TIMP-1, and TIMP-2 levels," Gerontology (2011) 57: 44-52).

Krementsov "A Martian Stranded on Earth: Alexander Bogdanov, Blood Transfusions, and Proletarian Science" pp. 57-59,85,86, and 88. University of Chicago Press, Chicago, United States, 2011.

Kwak et al., "Aging, exercise, and extracellular matrix in the heart." J Exerc Rehabil. Jun. 30, 2013;9(3):338-47.

Lee, et al., "Effects of aging on blood brain barrier and matrix metalloproteases following controlled cortical impact in mice," Experimental Neurology (2012) 234: 50-61).

Lin et al., "Discovery of a cytokine and its receptor by functional screening of the extracellular proteome." Science. May 9, 2008;320(5877):807-11.

Loffredo et al., "Growth differentiation factor 11 is a circulating factor that reverses age-related cardiac hypertrophy." Cell. May 9, 2013;153(4):828-39.

Luo et al. "Colony-stimulating factor 1 receptor (CSF1R) signaling in injured neurons facilitates protection and survival.", J. Exp. Med. (2013) 210(1):157-172.

Lysaght et al., "Beta-2 microglobulin removal during continuous ambulatory peritoneal dialysis (CAPD)." Perit Dial Int. 1989;9(1):29-35.

Malkki, H. "Ageing: Could young blood combat age-related cognitive decline?" Nat. Rev. Neurol. Jun. 2014;10(6):307.

Manzo et al., "Role of chemokines and chemokine receptors in regulating specific leukocyte trafficking in the immune/inflammatory response." Clin Exp Rheumatol. Jul.-Aug. 2003;21(4):501-8.

McLaurin et al., "Microglial pilgrimage to the brain." Nat Med. Dec. 2010;16(12):1380-1.

Middeldorp et al. "A young systemic environment reverses degeneration in a mouse model of Alzheimer's disease", Neuroscience 2012, Presentation Abstract, Oct. 16, 2012, 2 pages.

Mitrasinovic et al., "Microglia overexpressing the macrophage colony-stimulating factor receptor are neuroprotective in a microglial-hippocampal organotypic coculture system." J Neurosci. Apr. 27, 2005;25(17):4442-51.

Mizuno e al., "Interleukin-34 selectively enhances the neuroprotective effects of microglia to attenuate oligomeric amyloid-β neurotoxicity." Am J Pathol. Oct. 2011;179(4):2016-27.

Moore et al., "An Alternate Perspective on the Roles of TIMPs and MMPs in Pathology," The American Journal of Pathology (2012) 180: 12-16).

Murphy, "Tissue inhibitors of metalloproteinases," Genome Biology (2011) 12).

Palop et al., "A network dysfunction perspective on neurodegenerative diseases." Nature. Oct. 19, 2006;443(7113):768-73.

Prakasam et al., "Amyloid and Neurodegeneration: Alzheimer's Disease and Retinal Degeneration" Chapter 7, Handbook of Neurochemistry and Molecular Neurobiology, Lajtha ed., 2009, 131-163. (Year: 2009).

Ron-Harel et al. "Age-Dependent Spatial Memory Loss Can Be Partially Restored by Immune Activation", Rejuvenation Resarch (2008), 11(5):903-13.

Royer et al., "A novel antagonist of prostaglandin 02 blocks the locomotion of eosinophils and basophils." Eur J Clin nvesl. Sep. 2008;38(9):663-71.

Schwartz et al. "How Do Immune Cells Support and Shape the Brain in Health, Disease, and Aging?" The Journal of Neuroscience, Nov. 6, 2013, 33(45):17587-96.

Sellebjerg, et al., "Identification of new sensitive biomarkers for the in vivo response to interferon-beta treatment in multiple sclerosis using DNA-array evaluation." Eur J Neurol. Dec. 2009;16(12):1291-8.

Shin et al., "Association of Eotaxin gene family with asthma and serum total IgE." Hum Mol Genet. Jun. 1, 2003;12(11):1279-85.

Skovronsky et al., "Neurodegenerative diseases: new concepts of pathogenesis and their therapeutic implications." Annu Rev Pathol. 2006;1:151-70.

Smith et al., "β2-microglobulin is a systemic pro-aging factor that impairs cognitive function and neurogenesis." Nat Med. Aug. 2015;21(8):932-7.

Stetler-Sstevenson et al., "TIMP-2: an endogenous inhibitor of angiogenesis," Trends in Molecular Medicine (2005) 11: 97-103).

Stetler-Stevenson, "Tissue Inhibitors of Metalloproteinases in Cell Signaling," Science Signaling (2008) 1).

Strobel et al., "Chicago: The Vampire Principle—Young Blood Rejuvenates Aging Brain?", Alzheimer Research Forum (Nov. 2009), p. 1-3.

Stubbs et al., "Indomethacin causes prostaglandin 0(2)-like and eotaxin-like selective responses in eosinophils and basophils." J Bioi Chern. Jul. 19, 2002;277(29):26012-20.

Suzuki et al., "Beta2-microglobulin-selective adsorbent column (Lixelle) for the treatment of dialysis-related amyloidosis." Ther Apher Dial. Feb. 2003;7(1):104-7.

Teixeira, A.L. et al, "Increased serum levels of CCL 11/eotaxin in schizophrenia", Process in Neuro-Psychopharmacology & Biological Psychiatry, vol. 32, No. 3, pp. 710-714, 2008.

Thomson et al. "Young blood for a keener mind", NewScientist (2012), 216(2887): 10.

Villeda et al. "The aging systemic milieu negatively regulates neurogenesis and cognitive function", Nature, Aug. 31, 2011, 477(7362):90-4.

Villeda et al. "Young blood reverses age-related cognitive impairments", Neuroscience 2012, Presentation Abstract, Oct. 17, 2012, 2 pages.

Villeda et al. "Young blood reverses age-related impairments in cognitive function and synaptic plasticity in mice", Nat Med. (Jun. 2014), 20(6):659-63.

Villeda et al., "Changes in the systemic milieu modulate neurogenesis during aging" Abstract, 39th Annual Neuroscience Meeting, Chicago, IL, Society for Neuroscience, Oct. 2009, 1-2. (Year: 2009).

Villeda et al., Meeting Date, Past and Future Meetings, 39th Annual Neuroscience Meeting, Society for Neuroscience, 2009, 1. (Year: 2009).

Vincent et al., "Macrophage colony stimulating factor prevents NMDA-induced neuronal death in hippocampal organotypic cultures." J Neurochem. Sep. 2002;82(6):1388-97.

Visse et al. "Matrix Metalloproteinases and Tissue Inhibitors of Metalloproteinases," Circulation Research (2003) 92: 827-39).

Wang et al., "Expression of colony stimulating factor-1 receptor (CSF-1R) by CNS neurons in mice." J Neurosci Res. Sep. 1, 1999;57(5):616-32.

Wang et al., "Matrix metalloproteinases and their multiple roles in Alzheimer's disease." Biomed Res Int. 2014;2014:908636.

Website document entitled "Plasma Protein Composition" (available at http://www.sigmaaldrich science/metabolomics/enzyme-

(56) References Cited

OTHER PUBLICATIONS explorer/learning-center/plasma-blood-proteins/plasma-protein-composition.html). Downloaded from internet Jun. 27, 2017., 3 pages.

Wilson et al., "Beta2-microglobulin as a biomarker in peripheral arterial disease: proteomic profiling and clinical studies." Circulation. Sep. 18, 2007;116(12):1396-403.

Xu, et al., "Matrix Metalloproteinase Inhibitors: A review on Bioanalytical Methods, Pharmacokinetics and Metabolism," Current Drug Metabolism (2011) 12: 395-410).

Yagihashi A. et al., "Macrophage colony stimulating factor (M-CSF) protects spiral ganglion neurons following auditory nerve injury: morphological and functional evidence." Exp Neurol. Mar. 2005;192(1):167-77.

Yamane et al., "CSF-1 receptor-mediated differentiation of a new type of monocytic cell with B cell-stimulating activity: its selective dependence on IL-34." J Leukoc Biol. Jan. 2014;95(1):19-31.

Ye, et al., "Haptoglobin-alpha subunit as potential serum biomarker in ovarian cancer: identification and characterization using proteomic profiling and mass spectrometry." Clinical Cancer Research (Aug. 2003), 9 (8):2904-11.

SFN "Young blood can reverse some effects of ageing, study finds", Author Unknown, Society for Neuroscience, The Observer, Oct. 24, 2012, 2 pages, Retrieved online: http://gonzoj.wordpress.com/tag/society-for-neuroscience/.

Search Report dated Aug. 2, 2017, for related European application No. 14868769.2, 8 pages.

Search Report of related PCT/US2011/022916, dated Oct. 31, 2011, 11 pages.

Search Report of related PCT/US2014/068897, dated Feb. 27, 2015, 11 pages.

Search Report of related PCT/US2016/032907, dated Dec. 1, 2016, 24 pages.

Search Report of related PCT/US2016/036032, dated Feb. 21, 2017, 13 pages.

Search Report of related PCT/US2017/012521, dated Feb. 2, 2017, 12 pages.

Examiner Report of 2016265948, dated May 11, 2018, 6 pages.

Examiner Report of 738184, dated Apr. 6, 2018, 4 pages.

Giorgetti et al., "beta2-Microglobulin is potentially neurotoxic, but the blood brain barrier is likely to protect the brain from its toxicity." Nephrol Dial Transplant. Apr. 2009;24(4):1176-81.

Longo "Alzheimer's Prevention, Treatment and Research—A Q&A" Stanford Health Now, 2016, 1-2.

Perez-Martinez et al. "Tissue inhibitor of metalloproteinase-2 promotes neuronal differentiation by acting as an anti-mitogenic signal." J Neurosci. May 18, 2005;25(20):4917-29.

Martino et al., "Circulating MicroRNAs Are Not Eliminated by Hemodialysis" (2012) Circulating MicroRNAs Are Not Eliminated by Hemodialysis. PLOS ONE 7(6): e38269.

Niezgoda et al., "The effect of cladribine treatment on beta-2 microglobin in the cerebrospinal fluid and serum of patients with multiple sclerosis" Neurol Neurochir Pol. Mar.-Apr. 2000;34(2):281-7. (Abstract).

Reitz, "Toward precision medicine in Alzheimer's disease." Ann Transl Med. Mar. 2016;4(6):107.

Examiner Report of 720949, dated Jan. 18, 2019, 5 pages.

* cited by examiner

METHODS AND COMPOSITIONS FOR TREATING AGING-ASSOCIATED IMPAIRMENTS

CROSS-REFERENCE TO RELATED APPLICATIONS

This application is a U.S. 371 national phase entry of International Patent Application No. PCT/US2016/032907, filed May 17, 2016, which claims priority to the filing date of the U.S. Provisional Patent Application Ser. No. 62/163,222 filed May 18, 2015, the disclosure of which applications are incorporated herein by reference in their entireties.

This application is also a continuation-in-part application of U.S. patent application Ser. No. 14/280,939 filed on May 19, 2014; which application is a continuation application of U.S. patent application Ser. No. 13/575,437 filed on Oct. 9, 2012, now abandoned; which application is a United States national phase application of PCT Application Serial No. PCT/US2011/022916 filed on Jan. 28, 2011; which application, pursuant to 35 U.S.C. § 119 (e), claims priority to the filing date of the U.S. Provisional Patent Application Ser. No. 61/298,998 filed Jan. 28, 2010; the disclosures of which applications are incorporated herein by reference.

GOVERNMENT RIGHTS

This invention was made with Government support under contracts AG027505, OD012178, and TR000004 awarded by the National Institutes of Health. The Government has certain rights in the invention.

INTRODUCTION

Aging in an organism is accompanied by an accumulation of changes over time. In the nervous system, aging is accompanied by structural and neurophysiological changes that drive cognitive decline and susceptibility to degenerative disorders in healthy individuals. (Heeden & Gabrieli, "Insights into the ageing mind: a view from cognitive neuroscience," Nat. Rev. Neurosci. (2004) 5: 87-96; Raz et al., "Neuroanatomical correlates of cognitive aging: evidence from structural magnetic resonance imaging," Neuropsychology (1998) 12:95-114; Mattson & Magnus, "Ageing and neuronal vulnerability," Nat. Rev. Neurosci. (2006) 7: 278-294; and Rapp & Heindel, "Memory systems in normal and pathological aging," Curr. Opin. Neurol. (1994) 7:294-298). Included in these changes are synapse loss and the loss of neuronal function that results. Thus, although significant neuronal death is typically not observed during the natural aging process, neurons in the aging brain are vulnerable to sub-lethal age-related alterations in structure, synaptic integrity, and molecular processing at the synapse, all of which impair cognitive function.

In addition to the normal synapse loss during natural aging, synapse loss is an early pathological event common to many neurodegenerative conditions, and is the best correlate to the neuronal and cognitive impairment associated with these conditions. Indeed, aging remains the single most dominant risk factor for dementia-related neurodegenerative diseases such as Alzheimer's disease (AD) (Bishop et al., "Neural mechanisms of ageing and cognitive decline," Nature (2010) 464: 529-535 (2010); Heeden & Gabrieli, "Insights into the ageing mind: a view from cognitive neuroscience," Nat. Rev. Neurosci. (2004) 5:87-96; Mattson & Magnus, "Ageing and neuronal vulnerability," Nat. Rev. Neurosci. (2006) 7:278-294).

As human lifespan increases, a greater fraction of the population suffers from aging-associated cognitive impairments, making it crucial to elucidate means by which to maintain cognitive integrity by protecting against, or even counteracting, the effects of aging (Hebert et al., "Alzheimer disease in the US population: prevalence estimates using the 2000 census," Arch. Neurol. (2003) 60:1119-1122; Bishop et al., "Neural mechanisms of ageing and cognitive decline," Nature (2010) 464:529-535).

β-2 microglobulin (B2M) is a component of the class I major histocompatibility complex (MHC), a multi-protein complex found on the surface of nearly all nucleated mammalian cells. These complexes function by presenting foreign antigens or peptide fragments on the cell surface so that the immune system may recognize and destroy infected cells. The protein components of the class I MHC are encoded by several genes, each with multiple alleles, and the types of expressed class I MHC's vary among individuals. Because the MHC is polymorphic, it is an important factor for consideration during organ transplant as the host immune system may reject organs with foreign MHC's. In cancerous cells, MHC expression may be defective, allowing such cells to escape immune detection and destruction.

Free extracellular B2M is also found in human physiological fluids such as the blood serum, urine, and cerebral spinal fluid. Due to its small size, the protein is normally filtered from the blood and then reabsorbed in some amount by the kidney. High serum concentrations of B2M often accompany the presence of several diseases such as non-Hodgkin lymphoma and meningitis (Hallgren et al., "Lactoferrin, lysozyme, and beta 2-microglobulin levels in cerebrospinal fluid: differential indices of CNS inflammation," Inflammation (1982) 6:291-304; et al., "Prognostic significance of serum beta-2 microglobulin in patients with non-Hodgkin lymphoma," Oncology (2014) 87:40-7). When present in body serum at high concentrations, the protein can form amyloid fibrils (Corland & Heegaard, "B (2)-microglobulin amyloidosis," Sub-cellular Biochemistry (2012) 65:517-40). The buildup of B2M in body tissue and fluids as a complication of chronic kidney disease in individuals on dialysis has been extensively studied. In patients with reduced kidney function, buildup is associated with joint and bone weakness and pain. Urine B2M levels are measured to indicate kidney damage and filtration disorders (Acchiardo et al., "Beta 2-microglobulin levels in patients with renal insufficiency," American Journal of Kidney Diseases (1989) 13:70-4; Astor et al., "Serum Beta-2-microglobulin at discharge predicts mortality and graft loss following kidney transplantation," Kidney International (2013) 84:810-817).

Because protein aggregates of B2M play a role in provoking osteoarthritis, there is concern that the protein may be toxic to neuronal cells sensitive to abnormal protein deposits (Giorgetti et al., "beta2-Microglobulin is potentially neurotoxic, but the blood brain barrier is likely to protect the brain from its toxicity," Nephrology Dialysis Transplantation (2009) 24:1176-81). The protein has been implicated in neuronal development, normal hippocampus dependent memory and synapse formation and plasticity (Bilousova et al., "Major histocompatibility complex class I molecules modulate embryonic neuritogenesis and neuronal polarization," Journal of Neuroimmunology (2012) 247:1-8; Harrison et al., "Human brain weight is correlated with expression of the 'housekeeping genes' beta-2-microglobulin and TATA-binding protein," Neuropathology and Applied Neurobiology (2010) 36:498-504). Changes in proteins of the class I MHC such as beta 2 microglobulin could disrupt synaptic plasticity and lead to cognitive deficits in an aging, damaged, or diseased brain (Nelson et al., "MHC class I immune proteins are critical for hippocampus-dependent memory and gate NMDAR-dependent hippocampal long-term depression," Learning & Memory (2013) 20:505-17). A deficiency in B2M may also result in the loss of left-right asymmetries in the hippocampal region of the brain (Kawahara et al., "Neuronal major histocompatibility complex class I molecules are implicated in the generation of asymmetries in hippocampal circuitry," The Journal of Physiology (2013) 591:4777-91).

In addition, B2M serves as a molecular marker that can be used to determine immune compromise or central nervous system immune activation (Svatoňová et al., "Beta2-microglobulin as a diagnostic marker in cerebrospinal fluid: a follow-up study," Disease Markers (2014) 2014). Levels of the protein may signify the extent of the central nervous system inflammatory response. A review of B2M and its use as a disease marker states that elevated levels of B2M in the cerebral spinal fluid is reflective of multiple sclerosis, neuro-Behçet's disease, sarcoidosis, acquired immunodeficiency syndrome-dementia complex and meningeal metastasis of malignant tumors (Adachi, "Beta-2-microglobulin levels in the cerebrospinal fluid: their value as a disease marker. A review of the recent literature," European Neurology (1991) 31:181-5). Other studies suggest that B2M could potentially serve as a clinical marker for cognitive impairment risk or a tool for disease prognosis for individuals experiencing a range of diseases including kidney failure, HIV infection, and Alzheimer's (Almeida, "Cognitive impairment and major depressive disorder in HIV infection and cerebrospinal fluid biomarkers," Arquivos de Neuro-Psiquiatria (2013) 71:689-92; Annunziata et al., "Serum beta-2-microglobulin levels and cognitive function in chronic dialysis patients," Clinica Chimica Acta (1991) 201:139-41; Doecke et al., "Blood-based protein biomarkers for diagnosis of Alzheimer disease," Archives of Neurology (2012) 69:1318-25; Isshiki et al., "Cerebral blood flow in patients with peritoneal dialysis by an easy Z-score imaging system for brain perfusion single photon emission tomography," Therapeutic Apheresis and Dialysis (2014) 18:291-6). Elevated serum levels hold particular prognostic significance for adult multiple myeloma, lymphocytic leukemia and lymphoma (Kantarjian et al., "Prognostic significance of elevated serum beta 2-microglobulin levels in adult acute lymphocytic leukemia," The American Journal of Medicine (1992) 93:599-604; Wu et al., "Prognostic significance of serum beta-2 microglobulin in patients with non-Hodgkin lymphoma," Oncology (2014) 87:40-7). More studies continue to explore the implications of abnormal serum and tissue B2M levels for cancer, cardiovascular disease, schizophrenia, and systemic disease activity (Chittiprol et al., "Longitudinal study of beta2-microglobulin abnormalities in schizophrenia," International Immunopharmacology (2009) 9:1215-7). In some cases, B2M has been the target of disease therapies (Morabito et al., "Analysis and clinical relevance of human leukocyte antigen class I, heavy chain, and beta2-microglobulin down regulation in breast cancer," Human Immunology (2009) 70:492-5; Yang et al., "Identification of beta2-microglobulin as a potential target for ovarian cancer," Cancer Biology & Therapy (2009) 8:232-8).

SUMMARY

Methods of treating an adult mammal for an aging-associated impairment are provided. Aspects of the methods include reducing the β2-microglobulin (B2M) level in the mammal in a manner sufficient to treat the mammal for the aging-associated impairment. A variety of aging-associated impairments may be treated by practice of the methods, which impairments include cognitive impairments.

BRIEF DESCRIPTION OF THE FIGURES

FIGS. 1a & 1c, Schematic of unpaired young versus aged mice (FIG. 1a), and young isochronic versus heterochronic parabionts (FIG. 1c). FIGS. 1b & 1c, Changes in plasma concentration of B2M with age at 3, 6, 12, 18 and 24 months (FIG. 1b) and between young isochronic and young heterochronic parabionts five weeks after parabiosis (FIG. 1d). Data from 5 mice per group. FIGS. 1e & 1f, Changes in plasma (FIG. 1e; r=0.51; p<0.0001; 95% confidence interval=0.19-0.028) and CSF (FIG. 1f) B2M concentrations with age in healthy human subjects. FIGS. 1g & 1k, Young adult (3 months) mice were injected intraorbitally with B2M or PBS (vehicle) control five times over 12 days. FIG. 1g, Schematic of illustrating the chronological order used for B2M treatment and cognitive testing. FIGS. 1h & 1i, Hippocampal learning and memory was assessed by RAWM (FIG. 1h) and contextual fear conditioning (FIG. 1i). FIG. 1h, Number of entry arm errors prior to finding platform. i, Percent freezing time 24 h after training. Data from 9-10 mice per group. FIG. 1j, Representative field of Dcx-positive cells for each treatment group (scale bar: 100 μm). FIG. 1k, Quantification of neurogenesis in the dentate gyrus (DG) after treatment. Data from 7-8 mice per group. All data represented as dot plots with Mean or bar graphs with Mean±SEM; *P<0.05; P<0.01; *P<0.001 t-test (FIGS. 1d, 1f, 1i & 1k), ANOVA, Tukey's post-hoc test (FIG. 1b), Mann-Whitney U Test (e) and repeated measures ANOVA, Bonferroni post-hoc test (FIG. 1k).

FIGS. 2a-2e, Learning and memory was examined during normal aging in young (3-month-old) versus old (18-month-old) animals using RAWM (FIGS. 2a & 2b) and contextual fear conditioning (FIGS. 2c & 2e) paradigms. n=10 per group. FIG. 2a, Old mice demonstrate impaired learning and memory for platform location during the testing phase of the RAWM task. Cognitive deficits were quantified as the number of entry arm errors made prior to finding the target platform. FIG. 2b, No differences in swim speeds of were detected between young and old animals. FIG. 2c, Young and old animals exhibited similar baseline freezing time during fear conditioning training. FIG. 2d, During contextual fear conditioning old mice demonstrate decreased freezing time during contextual memory testing. FIG. 2e, No differences in cued memory were detected 24 hours after training. Data represented as mean±s.e.m.; *P<0.05; **P<0.01; n.s., not significant; t-test (FIGS. 2a-2c & 2e), repeated measures ANOVA, Bonferroni post-hoc test (FIG. 2d).

FIGS. 3a-3d, Young adult (3 months) mice were injected intraorbitally with B2M or PBS (vehicle) control five times over 10 days prior to behavioral testing. FIG. 3a, Average mouse weight of B2M and vehicle treated groups. FIG. 3b, Swim speeds of mice injected with B2M or vehicle during the testing phase of the RAWM. FIGS. 3c & 3d, Conditioned fear was displayed as freezing behavior. FIG. 3c, Animals from all treatment groups exhibited similar baseline freezing time during training. FIG. 3d, No differences in cued memory were detected between groups when re-exposed to the conditioned stimulus (tone and light) in a novel context 24 hours after training. Data from 9 mice per group. All data represented as Mean+SEM; n.s. not significant; t-test.

FIGS. 4a & 4b, Young adult mice (3-4 months) were injected with B2M or PBS (vehicle) control through intraorbital injections five times over 12 days. Prior to euthanasia Bromodeoxyuridne (BrdU) was administered by intraperitoneal injections for three days. Quantification of MCM2-positive and BrdU-positive in the dentate gyrus (DG) after treatment. Data from 5 mice per group. All data represented as Mean+SEM; *P<0.05; **P<0.01; t-test.

FIGS. 5a & 5b, Representative Western blot and quantification of hippocampal lysates probed with anti-B2M and anti-Actin antibodies from young (3 months) and old (18 months) unpaired animals (FIG. 5a), or young isochronic and young heterochronic parabionts five weeks after parabiosis (FIG. 5b). FIGS. 5c-5e, Young adult (3 months) wild type (WT) and transporter associated with antigen processing 1 knock out (Tap1−/−) mice were given unilateral stereotaxic injections of B2M or vehicle control FIG. 5c, Representative field of Dcx-positive cells in adjacent sides of the DG within the same section are shown for WT and Tap1−/− treatment groups. FIGS. 5d & 5e, Quantification of neurogenesis in the DG of WT (d) and Tap1−/− (FIG. 5e) mice after stereotaxic B2M administration. Data from five mice per group. FIGS. 5f-5h, Young adult mice were given bilateral stereotaxic injections of B2M or vehicle six days prior to behavioral testing. FIG. 5f, Schematic illustrating chronological order used for local B2M administration and cognitive testing. FIGS. 5g & 5h, Learning and memory was assessed by RAWM (FIG. 5h) and contextual fear conditioning (FIG. 5g) following stereotaxic injections. Data from 10 animals per group. All data represented as Mean±SEM; *P<0.05; **P<0.01; n.s. not significant; ANOVA, t-test (FIGS. 5a,5b, 5d,5e & 5h); repeated measures ANOVA, Bonferroni post-hoc test (FIG. 5g).

FIGS. 6a-6c, Young adult mice were given bilateral stereotaxic injections of B2M or PBS (vehicle) control six days prior to behavioral testing. FIG. 6a, Swim speeds of mice injected with B2M or vehicle during the testing phase of the RAWM. FIG. 6b, Animals from all treatment groups exhibited similar baseline freezing time during fear conditioning training. FIG. 6c, No differences in cued memory were detected between groups when re-exposed to the conditioned stimulus (tone and light) in a novel context 24 hours after training. Data from 10 mice per group. All data represented as Mean+SEM; n.s. not significant; t-test.

FIG. 7a, Quantification of Doublecortin (Dcx)-positive cells in the DG of young adult (3 months) wild type (WT) and Tap1−/− unpaired mice. Data from 5 mice per group. FIG. 7b, Schematic of young WT and Tap1−/− isochronic parabionts. FIGS. 7c-7e, Quantification of Dcx, T-box transcription factor Tbr2, and BrdU immunostaining of young WT and Tap1−/− isochronic parabionts five weeks after parabiosis. Data from 6-8 mice per group. All data represented as Mean+SEM; n.s. not significant; t-test (FIG. 7a); ANOVA, Tukey's post-hoc test (FIGS. 7c-7e).

FIG. 8a, Schematic of young wild type (WT) and Tap1 knock out (Tap1−/−) isochronic parabionts and young WT and Tap1−/− heterochronic parabionts. FIGS. 8b & 8c Representative fields (FIG. 8b) and quantification (FIG. 8c) of Doublecortin immunostaining of young isochronic and heterochronic parabionts five weeks after parabiosis (arrowheads point to individual cells, scale bar: 100 μm). FIG. 8d, Prior to euthanasia animals were injected with Bromodeoxyuridne (BrdU) for three days, and proliferating cells having incorporated BrdU were quantified in DG after parabiosis. Data from 8 young isochronic WT, 6 young isochronic Tap1−/−, 8 young heterochronic WT, and 8 young heterochronic Tap1−/− parabionts. All data represented as Mean±SEM; *P<0.05; ANOVA, Tukey's post-hoc test.

FIG. 9a, Schematic of young wild type (WT) and Tap1 knock out (Tap1−/−) isochronic parabionts and young WT and Tap1−/− heterochronic parabionts. FIG. 9b, Quantification of the T-box transcription factor Tbr2 immunostaining of young isochronic and heterochronic parabionts five weeks after parabiosis Data from 8 young isochronic WT, 6 young isochronic Tap1−/−, 8 young heterochronic WT, and 8 young heterochronic Tap1−/− parabionts. All data represented as Mean±SEM; *P<0.05; ANOVA, Tukey's post-hoc test.

FIGS. 10a-10d, Learning and memory was assessed in young (3 months) and old (15-16 months) wild type (WT) and B2M knock out (B2M−/−) mice by RAWM (FIGS. 10a, 10c) and contextual fear conditioning (FIGS. 10b & 10d). Data from 10 young and 8-12 old mice per genotype. FIGS. 10e-10j, Neurogenesis was analyzed by immunostaining for Dcx-positive cells in the DG of young and old WT and B2M−/− mice. Representative field and quantification of Dcx-positive cells are shown for young (FIGS. 10e & 10f) and old (FIGS. 10e & 10g) WT and B2M−/− animals (arrowheads point to individual immature neurons, scale bar: 100 μm). Data from 8 young and 10 old mice per genotype. FIGS. 10h & 10j, WT and B2M−/− mice were administered BrdU by intraperitoneal injections for six days and euthanized 28 days later. FIG. 10h, Representative confocal microscopy from the DG of brain sections immunostained for BrdU (red) in combination with NeuN (green). FIGS. 10i & 10j, Quantification of the relative number of BrdU and NeuN-double positive cells out of the total BrdU-positive cells in the young (FIG. 10i) and old (FIG. 10j) DG of WT and B2M−/− animals. Data from 8 mice per group (3 sections per mouse). All data represented as Mean±SEM; *P<0.05; **P<0.01; n.s. not significant; t-test (FIGS. 10b, 10d, 10f, 10i, 10j); repeated measures ANOVA, Bonferroni post-hoc test (FIG. 10a, FIG. 10c).

FIGS. 11a-11f, Hippocampal learning and memory was assessed old adult (17 months) WT and during the testing phase of the RAWM. Animals exhibited similar baseline freezing time during fear conditioning training regardless of genotype. No differences in cued memory were detected between genotypes when mice were re-exposed to the conditioned stimulus (tone and light) in a novel context 24 hours after training. Data from 12 WT and 8 B2M−/− mice. All data represented as Mean+SEM; n.s. not significant; t-test.

FIGS. 12a-12c, To assess proliferation young (3 months) and old (15-16 months) wild type (WT) and B2M knock out (B2M−/−) mice were administered BrdU by intraperitoneal injections for three days prior to euthanasia. FIGS. 12b & 12c, Immunostaining of BrdU-positive cells was quantified in the DG of young (FIG. 12b) and old (FIG. 12c) animals. Data from 8 young and 10 old mice per genotype. FIGS. 12c-12e, For examine astrocyte differentiation WT and B2M−/− mice were administered BrdU by intraperitoneal injections for six days and euthanized 28 days later. FIG. 12c, Representative confocal microscopy from the DG of brain sections immunostained for BrdU (red) in combination with GFAP (blue). FIGS. 12d & 12e, Quantification of the relative number of BrdU and GFAP-double positive cells out of the total BrdU-positive cells in the young (FIG. 12d) and old (FIG. 12e) DG of WT and B2M−/− animals. Data from 8 mice per group (3 sections per mouse). All data represented as Mean+SEM; **P<0.01; n.s. not significant; t-test.

DETAILED DESCRIPTION

Figure 1:
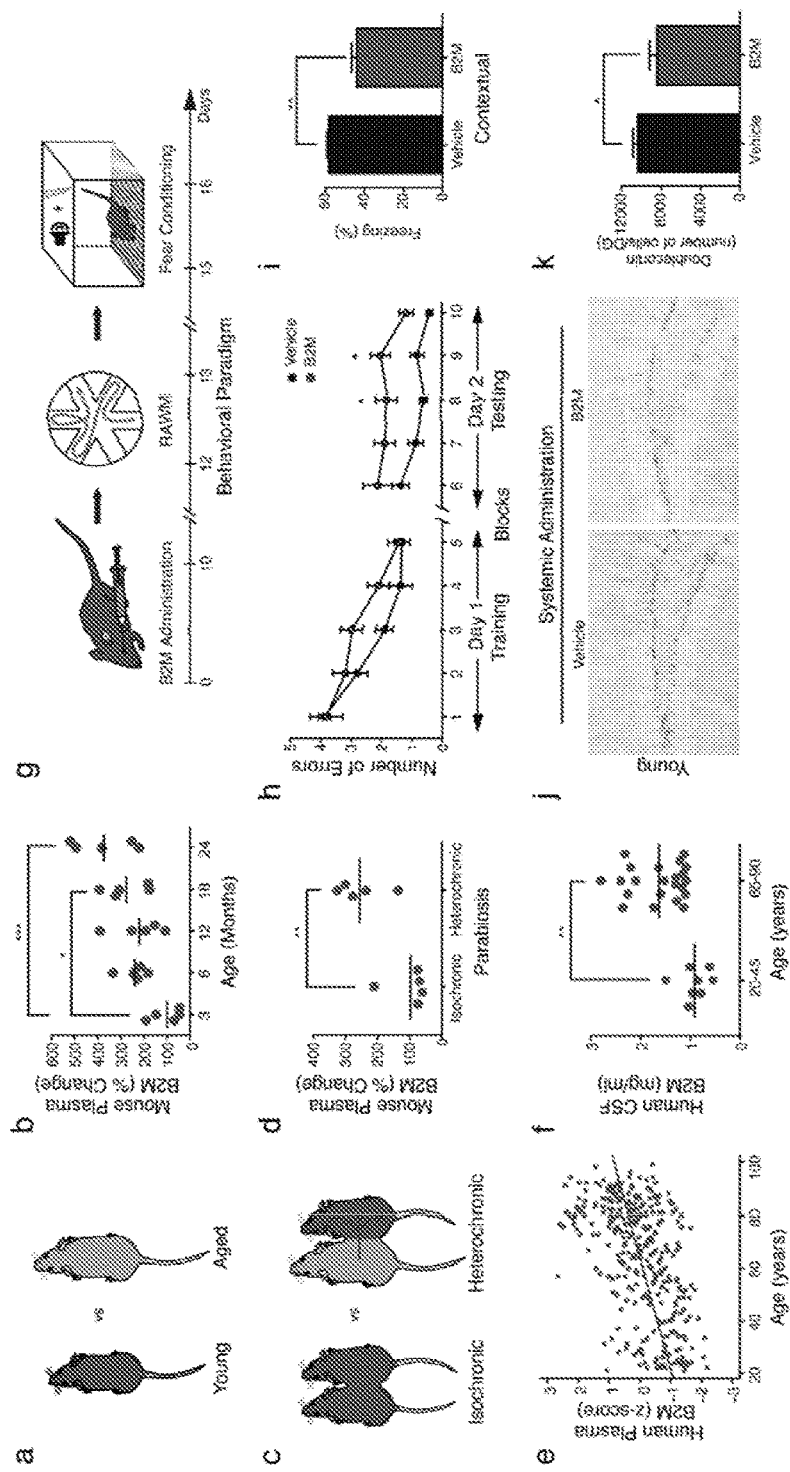
FIGS. 1a-1k. B2M is a component of the aging systemic environment that impairs hippocampal-dependent cognitive function and adult neurogenesis.
Figure 2:
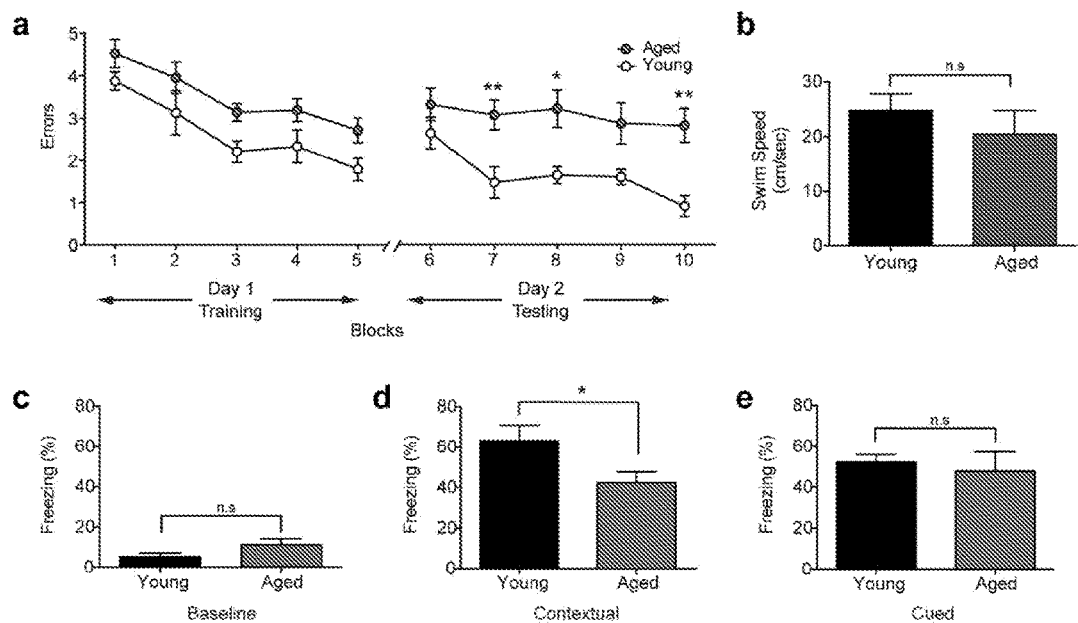
FIGS. 2a-2e. Hippocampal dependent learning and memory.

Methods of treating an adult mammal for an aging-associated impairment are provided. Aspects of the methods include reducing the β2-microglobulin (B2M) level in the mammal in a manner sufficient to treat the mammal for the aging-associated impairment. A variety of aging-associated impairments may be treated by practice of the methods, which impairments include cognitive impairments.

Before the present methods and compositions are described, it is to be understood that this invention is not limited to a particular method or composition described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

It must be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g., polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Methods

As summarized above, aspects of the invention include methods of treating an aging-associated impairment in an adult mammal. The aging-associated impairment may manifest in a number of different ways, e.g., as aging-associated cognitive impairment and/or physiological impairment, e.g., in the form of damage to central or peripheral organs of the body, such as but not limited to: cell injury, tissue damage, organ dysfunction, aging-associated lifespan shortening and carcinogenesis, where specific organs and tissues of interest include, but are not limited to skin, neuron, muscle, pancreas, brain, kidney, lung, stomach, intestine, spleen, heart, adipose tissue, testes, ovary, uterus, liver and bone; in the form of decreased neurogenesis, etc.

In some embodiments, the aging-associated impairment is an aging-associated impairment in cognitive ability in an individual, i.e., an aging-associated cognitive impairment. By cognitive ability, or "cognition", it is meant the mental processes that include attention and concentration, learning complex tasks and concepts, memory (acquiring, retaining, and retrieving new information in the short and/or long term), information processing (dealing with information gathered by the five senses), visuospatial function (visual perception, depth perception, using mental imagery, copying drawings, constructing objects or shapes), producing and understanding language, verbal fluency (word-finding), solving problems, making decisions, and executive functions (planning and prioritizing). By "cognitive decline", it is meant a progressive decrease in one or more of these abilities, e.g., a decline in memory, language, thinking, judgment, etc. By "an impairment in cognitive ability" and "cognitive impairment", it is meant a reduction in cognitive ability relative to a healthy individual, e.g., an age-matched healthy individual, or relative to the ability of the individual at an earlier point in time, e.g., 2 weeks, 1 month, 2 months, 3 months, 6 months, 1 year, 2 years, 5 years, or 10 years or more previously. Aging-associated cognitive impairments include impairments in cognitive ability that are typically associated with aging, including, for example, cognitive impairment associated with the natural aging process, e.g., mild cognitive impairment (M.C.I.); and cognitive impairment associated with an aging-associated disorder, that is, a disorder that is seen with increasing frequency with increasing senescence, e.g., a neurodegenerative condition such as Alzheimer's disease, Parkinson's disease, frontotemporal dementia, Huntington's disease, amyotrophic lateral sclerosis, multiple sclerosis, glaucoma, myotonic dystrophy, vascular dementia, and the like.

By "treatment" it is meant that at least an amelioration of one or more symptoms associated with an aging-associated impairment afflicting the adult mammal is achieved, where amelioration is used in a broad sense to refer to at least a reduction in the magnitude of a parameter, e.g., a symptom associated with the impairment being treated. As such, treatment also includes situations where a pathological condition, or at least symptoms associated therewith, are completely inhibited, e.g., prevented from happening, or stopped, e.g., terminated, such that the adult mammal no longer suffers from the impairment, or at least the symptoms that characterize the impairment. In some instances, "treatment", "treating" and the like refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" may be any treatment of a disease in a mammal, and includes: (a) preventing the disease from occurring in a subject which may be predisposed to the disease but has not yet been diagnosed as having it; (b) inhibiting the disease, i.e., arresting its development; or (c) relieving the disease, i.e., causing regression of the disease. Treatment may result in a variety of different physical manifestations, e.g., modulation in gene expression, increased neurogenesis, rejuvenation of tissue or organs, etc. Treatment of ongoing disease, where the treatment stabilizes or reduces the undesirable clinical symptoms of the patient, occurs in some embodiments. Such treatment may be performed prior to complete loss of function in the affected tissues. The subject therapy may be administered during the symptomatic stage of the disease, and in some cases after the symptomatic stage of the disease.

In some instances where the aging-associated impairment is aging-associated cognitive decline, treatment by methods of the present disclosure slows, or reduces, the progression of aging-associated cognitive decline. In other words, cognitive abilities in the individual decline more slowly, if at all, following treatment by the disclosed methods than prior to or in the absence of treatment by the disclosed methods. In some instances, treatment by methods of the present disclosure stabilizes the cognitive abilities of an individual. For example, the progression of cognitive decline in an individual suffering from aging-associated cognitive decline is halted following treatment by the disclosed methods. As another example, cognitive decline in an individual, e.g., an individual 40 years old or older, that is projected to suffer from aging-associated cognitive decline, is prevented following treatment by the disclosed methods. In other words, no (further) cognitive impairment is observed. In some instances, treatment by methods of the present disclosure reduces, or reverses, cognitive impairment, e.g., as observed by improving cognitive abilities in an individual suffering from aging-associated cognitive decline. In other words, the cognitive abilities of the individual suffering from aging-associated cognitive decline following treatment by the disclosed methods are better than they were prior to treatment by the disclosed methods, i.e., they improve upon treatment. In some instances, treatment by methods of the present disclosure abrogates cognitive impairment. In other words, the cognitive abilities of the individual suffering from aging-associated cognitive decline are restored, e.g., to their level when the individual was about 40 years old or less, following treatment by the disclosed methods, e.g., as evidenced by improved cognitive abilities in an individual suffering from aging-associated cognitive decline.

In some instances, treatment of an adult mammal in accordance with the methods results in a change in a central organ, e.g., a central nervous system organ, such as the brain, spinal cord, etc., where the change may manifest in a number of different ways, e.g., as described in greater detail below, including but not limited to molecular, structural and/or functional, e.g., in the form of enhanced neurogenesis.

As summarized above, methods described herein are methods of treating an aging-associated impairment, e.g., as described above, in an adult mammal. By adult mammal is meant a mammal that has reached maturity, i.e., that is fully developed. As such, adult mammals are not juvenile. Mammalian species that may be treated with the present methods include canines and felines; equines; bovines; ovines; etc., and primates, including humans. The subject methods, compositions, and reagents may also be applied to animal models, including small mammals, e.g., murine, lagomorpha, etc., for example, in experimental investigations. The discussion below will focus on the application of the subject methods, compositions, reagents, devices and kits to humans, but it will be understood by the ordinarily skilled artisan that such descriptions can be readily modified to other mammals of interest based on the knowledge in the art.

The age of the adult mammal may vary, depending on the type of mammal that is being treated. Where the adult mammal is a human, the age of the human is generally 18 years or older. In some instances, the adult mammal is an individual suffering from or at risk of suffering from an aging-associated impairment, such as an aging-associated cognitive impairment, where the adult mammal may be one that has been determined, e.g., in the form of receiving a diagnosis, to be suffering from or at risk of suffering from an aging-associated impairment, such as an aging-associated cognitive impairment. The phrase "an individual suffering from or at risk of suffering from an aging-associated cognitive impairment" refers to an individual that is about 50 years old or older, e.g., 60 years old or older, 70 years old or older, 80 years old or older, and sometimes no older than 100 years old, such as 90 years old, i.e., between the ages of about 50 and 100, e.g., 50, 55, 60, 65, 70, 75, 80, 85 or about 90 years old. The individual may suffer from an aging associated condition, e.g., cognitive impairment, associated with the natural aging process, e.g., M.C.I. Alternatively, the individual may be 50 years old or older, e.g., 60 years old or older, 70 years old or older, 80 years old or older, 90 years old or older, and sometimes no older than 100 years old, i.e., between the ages of about 50 and 100, e.g., 50, 55, 60, 65, 70, 75, 80, 85, 90, 95 or about 100 years old, and has not yet begun to show symptoms of an aging associated condition, e.g., cognitive impairment. In yet other embodiments, the individual may be of any age where the individual is suffering from a cognitive impairment due to an aging-associated disease, e.g., Alzheimer's disease, Parkinson's disease, frontotemporal dementia, Huntington's disease, amyotrophic lateral sclerosis, multiple sclerosis, glaucoma, myotonic dystrophy, dementia, and the like. In some instances, the individual is an individual of any age that has been diagnosed with an aging-associated disease that is typically accompanied by cognitive impairment, e.g., Alzheimer's disease, Parkinson's disease, frontotemporal dementia, progressive supranuclear palsy, Huntington's disease, amyotrophic lateral sclerosis, spinal muscular atrophy, multiple sclerosis, multi-system atrophy, glaucoma, ataxias, myotonic dystrophy, dementia, and the like, where the individual has not yet begun to show symptoms of cognitive impairment.

As summarized above, aspects of the methods include reducing the β2-microglobulin (B2M) level in the mammal in a manner sufficient to treat the aging impairment in the mammal, e.g., as described above. By reducing the B2M level is meant lowering the amount of B2M in the mammal, such as the amount of extracellular B2M in the mammal. While the magnitude of the reduction may vary, in some instances the magnitude is 2-fold or greater, such as 5-fold or greater, including 10-fold or greater, e.g., 15-fold or greater, 20-fold or greater, 25-fold or greater (as compared to a suitable control), where in some instances the magnitude is such that the amount of detectable free B2M in the circulatory system of the individual is 50% or less, such as 25% or less, including 10% or less, e.g., 1% or less, relative to the amount that was detectable prior to intervention according to the invention, and in some instances the amount is undetectable following intervention.

The B2M level may be reduced using any convenient protocol. In some instances, the B2M level is reduced by removing systemic B2M from the adult mammal, e.g., by removing B2M from the circulatory system of the adult mammal. In such instances, any convenient protocol for removing circulatory B2M may be employed. For example, blood may be obtained from the adult mammal and extracorporeally processed to remove B2M from the blood to produce B2M depleted blood, which resultant B2M depleted blood may then be returned to the adult mammal. Such protocols may employ a variety of different techniques in order to remove B2M from the obtained blood. For example, the obtained blood may be contacted with a filtering component, e.g., a membrane, etc., which allows passage of B2M but inhibits passage of other blood components, e.g., cells, etc. In some instances, the obtained blood may be contacted with a B2M absorptive component, e.g., porous bead or particulate composition, which absorbs B2M from the blood. In yet other instances, the obtained blood may be contacted with a B2M binding member stably associated with a solid support, such that B2M binds to the binding member and is thereby immobilized on the solid support, thereby providing for separation of B2M from other blood constituents. The protocol employed may or may not be configured to selectively remove B2M from the obtained blood, as desired. A number of different technologies are known for removing B2M from blood, and may be employed in embodiments of the invention, where such technologies include those described in U.S. Pat. Nos. 4,872,983; 5,240,614; 6,416,487; 6,419,830; 6,423,024; 6,855,121; 7,066,900; 8,211,310; 8,349,550; as well as published United States Patent Application Publication No. 20020143283 and published PCT Application Publication Nos.: WO/1999/006098 and WO/2003/020403; the disclosures of which applications are herein incorporated by reference.

In some embodiments, the B2M level is reduced by administering to the mammal an effective amount of a B2M level reducing agent. As such, in practicing methods according to these embodiments of the invention, an effective amount of the active agent, e.g., B2M modulatory agent, is provided to the adult mammal.

Depending on the particular embodiments being practiced, a variety of different types of active agents may be employed. In some instances, the agent modulates expression of the RNA and/or protein from the gene, such that it changes the expression of the RNA or protein from the target gene in some manner. In these instances, the agent may change expression of the RNA or protein in a number of different ways. In certain embodiments, the agent is one that reduces, including inhibits, expression of a B2M protein. Inhibition of B2M protein expression may be accomplished using any convenient means, including use of an agent that inhibits B2M protein expression, such as, but not limited to: RNAi agents, antisense agents, agents that interfere with a transcription factor binding to a promoter sequence of the B2M gene, or inactivation of the B2M gene, e.g., through recombinant techniques, etc.

For example, the transcription level of a B2M protein can be regulated by gene silencing using RNAi agents, e.g., double-strand RNA (see e.g., Sharp, Genes and Development (1999) 13: 139-141). RNAi, such as double-stranded RNA interference (dsRNAi) or small interfering RNA (siRNA), has been extensively documented in the nematode *C. elegans* (Fire, et al, Nature (1998) 391:806-811) and routinely used to "knock down" genes in various systems. RNAi agents may be dsRNA or a transcriptional template of the interfering ribonucleic acid which can be used to produce dsRNA in a cell. In these embodiments, the transcriptional template may be a DNA that encodes the interfering ribonucleic acid. Methods and procedures associated with RNAi are also described in published PCT Application Publication Nos. WO 03/010180 and WO 01/68836, the disclosures of which applications are incorporated herein by reference. dsRNA can be prepared according to any of a number of methods that are known in the art, including in vitro and in vivo methods, as well as by synthetic chemistry approaches. Examples of such methods include, but are not limited to, the methods described by Sadher et al., Biochem. Int. (1987) 14:1015; Bhattacharyya, Nature (1990) 343:484; and U.S. Pat. No. 5,795,715, the disclosures of which are incorporated herein by reference. Single-stranded RNA can also be produced using a combination of enzymatic and organic synthesis or by total organic synthesis. The use of synthetic chemical methods enable one to introduce desired modified nucleotides or nucleotide analogs into the dsRNA. dsRNA can also be prepared in vivo according to a number of established methods (see, e.g., Sambrook, et al. (1989) Molecular Cloning: A Laboratory Manual, 2nd ed.; Transcription and Translation (B. D. Hames, and S. J. Higgins, Eds., 1984); DNA Cloning, volumes I and II (D. N. Glover, Ed., 1985); and Oligonucleotide Synthesis (M. J. Gait, Ed., 1984, each of which is incorporated herein by reference). A number of options can be utilized to deliver the dsRNA into a cell or population of cells such as in a cell culture, tissue, organ or embryo. For instance, RNA can be directly introduced intracellularly. Various physical methods are generally utilized in such instances, such as administration by microinjection (see, e.g., Zernicka-Goetz, et al. Development (1997) 124:1133-1137; and Wianny, et al., Chromosoma (1998) 107: 430-439). Other options for cellular delivery include permeabilizing the cell membrane and electroporation in the presence of the dsRNA, liposome-mediated transfection, or transfection using chemicals such as calcium phosphate. A number of established gene therapy techniques can also be utilized to introduce the dsRNA into a cell. By introducing a viral construct within a viral particle, for instance, one can achieve efficient introduction of an expression construct into the cell and transcription of the RNA encoded by the construct. Specific examples of RNAi agents that may be employed to reduce B2M expression include, but are not limited to: dsRNA and short interfering RNA (siRNA) corresponding to B2M with the following sense and antisense sequences (sense) 5'-GAUUCAG-GUUUACUCACGUdTdT-3' (SEQ ID NO:01) and (antisense) 5'-ACGUGAGUAAACCUGAAUCdTdT-3' (SEQ ID NO:02)(as described in Matin, et al., "Specific knockdown of Oct4 and beta2-microglobulin expression by RNA interference in human embryonic stem cells and embryonic carcinoma cells," Stem Cells (2004) 22: 659-68) and WO/2004/085654; shRNA (GCCACTCCCACCCTTTCT-CAT)(SEQ ID NO:03) (as disclosed in Goyos, et al., "Involvement of nonclassical MHC class Ib molecules in heat shock protein-mediated anti-tumor responses," (2007) 37: 1494-501); as well as the RNAi agents disclosed in Figueiredo, et al., "Generation of HLA-deficient platelets from hematopoietic progenitor cells," Transfusion (2010) 50: 1690-701, Bhatt, et al., "Knockdown of beta2-microglobulin perturbs the subcellular distribution of HFE and hepcidin," Biochemical and Biophysical Research Communications (2009) 378: 727-31, Elders, et al., "Targeted knockdown of canine KIT (stem cell factor receptor) using RNA interference," Veterinary Immunology and Immunopathology (2011) 141:151-6, Heikkila, et al., "Internalization of coxsackievirus A9 is mediated by beta 2-microglobulin, dynamin, and Arf6 but not by caveolin-1 or clathrin," (2010) 84: 3666-81, Figueiredo, et al., "Class-, gene-, and group-specific HLA silencing by lentiviral shRNA delivery (2006) 84: 425-37, WO/2004/020586, US20040127445 and US20130096370.

In some instances, antisense molecules can be used to down-regulate expression of a B2M gene in the cell. The anti-sense reagent may be antisense oligodeoxynucleotides (ODN), particularly synthetic ODN having chemical modifications from native nucleic acids, or nucleic acid constructs that express such anti-sense molecules as RNA. The antisense sequence is complementary to the mRNA of the targeted protein, and inhibits expression of the targeted protein. Antisense molecules inhibit gene expression through various mechanisms, e.g., by reducing the amount of mRNA available for translation, through activation of RNAse H, or steric hindrance. One or a combination of antisense molecules may be administered, where a combination may include multiple different sequences.

Antisense molecules may be produced by expression of all or a part of the target gene sequence in an appropriate vector, where the transcriptional initiation is oriented such that an antisense strand is produced as an RNA molecule. Alternatively, the antisense molecule is a synthetic oligonucleotide. Antisense oligonucleotides will generally be at least about 7, usually at least about 12, more usually at least about 20 nucleotides in length, and not more than about 500, usually not more than about 50, more usually not more than about 35 nucleotides in length, where the length is governed by efficiency of inhibition, specificity, including absence of cross-reactivity, and the like. Short oligonucleotides, of from 7 to 8 bases in length, can be strong and selective inhibitors of gene expression (see Wagner et al., Nature Biotechnol. (1996) 14:840-844).

A specific region or regions of the endogenous sense strand mRNA sequence are chosen to be complemented by the antisense sequence. Selection of a specific sequence for the oligonucleotide may use an empirical method, where several candidate sequences are assayed for inhibition of expression of the target gene in an in vitro or animal model. A combination of sequences may also be used, where several regions of the mRNA sequence are selected for antisense complementation.

Antisense oligonucleotides may be chemically synthesized by methods known in the art (see Wagner et al. (1993), supra.) Oligonucleotides may be chemically modified from the native phosphodiester structure, in order to increase their intracellular stability and binding affinity. A number of such modifications have been described in the literature, which alter the chemistry of the backbone, sugars or heterocyclic bases. Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O-5'-S-phosphorothioate, 3'-S-5'-O-phosphorothioate, 3'-CH.sub.2-5'-O-phosphonate and 3'-NH-5'-O-phosphoroamidate. Peptide nucleic acids replace the entire ribose phosphodiester backbone with a peptide linkage. Sugar modifications are also used to enhance stability and affinity. The α-anomer of deoxyribose may be used, where the base is inverted with respect to the natural β-anomer. The 2'-OH of the ribose sugar may be altered to form 2'-O-methyl or 2'-O-allyl sugars, which provides resistance to degradation without comprising affinity. Modification of the heterocyclic bases must maintain proper base pairing. Some useful substitutions include deoxyuridine for deoxythymidine; 5-methyl-2'-deoxycytidine and 5-bromo-2'-deoxycytidine for deoxycytidine. 5-propynyl-2'-deoxyuridine and 5-propynyl-2'-deoxycytidine have been shown to increase affinity and biological activity when substituted for deoxythymidine and deoxycytidine, respectively. Specific examples of antisense agents that may be employed to reduce B2M expression include, but are not limited to:

| Code | Oligonucleotide |
| --- | --- |
| MB-00027 | βA*βG*dT*dT*dG*dC*dC*dA*dG*dC*dC*dC*dT*βZ*βZ |
| MB-00540 | Eru*SS*βA*βG*dT*dT*dG*dC*dC*dA*dG*dC*dC*dC*dT*βZ*βZ |
| MB-00541 | Myr*SS*βA*βG*dT*dT*dG*dC*dC*dA*dG*dC*dC*dC*dT*βZ*βZ |
| MB-00542 | Dier*SS*βA*βG*dT*dT*dG*dC*dC*dA*dG*dC*dC*dC*dT*βZ*βZ |
| MB-00543 | Ermy*SS*βA*βG*dT*dT*dG*dC*dC*dA*dG*dC*dC*dC*dT*βZ*βZ |

(SEQ ID NOS: 04 to 08)

as described in WO/2004/004575; as well as those antisense agents described in: Lichtenstein, et al., "Effects of beta-2 microglobulin anti-sense oligonucleotides on sensitivity of HER2/neu oncogene-expressing and nonexpressing target cells to lymphocyte-mediated lysis," Cell Immunology (1992) 141: 219-32, Ogretmen, et al., "Molecular mechanisms of loss of beta 2-microglobulin expression in drug-resistant breast cancer sublines and its involvement in drug resistance," Biochemistry (1998) 37: 11679-91, WO/2004/020586; WO/2006/130949; U.S. Pat. Nos. 7,553,484; and 8,715,654.

As an alternative to anti-sense inhibitors, catalytic nucleic acid compounds, e.g. ribozymes, anti-sense conjugates, etc. may be used to inhibit gene expression. Ribozymes may be synthesized in vitro and administered to the patient, or may be encoded on an expression vector, from which the ribozyme is synthesized in the targeted cell (for example, see International patent application WO 9523225, and Beigelman et al. Nucl. Acids Res. (1995) 23:4434-42). Examples of oligonucleotides with catalytic activity are described in WO 9506764. Conjugates of anti-sense ODN with a metal complex, e.g. terpyridylCu(II), capable of mediating mRNA hydrolysis are described in Bashkin et al. Appl. Biochem. Biotechnol. (1995) 54:43-56.

In another embodiment, the B2M gene is inactivated so that it no longer expresses a functional protein. By inactivated is meant that the gene, e.g., coding sequence and/or regulatory elements thereof, is genetically modified so that it no longer expresses a functional B2M protein, e.g., at least with respect to B2M aging impairment activity. The alteration or mutation may take a number of different forms, e.g., through deletion of one or more nucleotide residues, through exchange of one or more nucleotide residues, and the like. One means of making such alterations in the coding sequence is by homologous recombination. Methods for generating targeted gene modifications through homologous recombination are known in the art, including those described in: U.S. Pat. Nos. 6,074,853; 5,998,209; 5,998,144; 5,948,653; 5,925,544; 5,830,698; 5,780,296; 5,776,744; 5,721,367; 5,614,396; 5,612,205; the disclosures of which are herein incorporated by reference.

Also of interest in certain embodiments are dominant negative mutants of B2M proteins, where expression of such mutants in the cell result in a modulation, e.g., decrease, in B2M mediated aging impairment. Dominant negative mutants of B2M are mutant proteins that exhibit dominant negative B2M activity. As used herein, the term "dominant-negative B2M activity" or "dominant negative activity" refers to the inhibition, negation, or diminution of certain particular activities of B2M, and specifically to B2M mediated aging impairment. Dominant negative mutations are readily generated for corresponding proteins. These may act by several different mechanisms, including mutations in a substrate-binding domain; mutations in a catalytic domain; mutations in a protein binding domain (e.g., multimer forming, effector, or activating protein binding domains); mutations in cellular localization domain, etc. A mutant polypeptide may interact with wild-type polypeptides (made from the other allele) and form a non-functional multimer. In certain embodiments, the mutant polypeptide will be overproduced. Point mutations are made that have such an effect. In addition, fusion of different polypeptides of various lengths to the terminus of a protein, or deletion of specific domains can yield dominant negative mutants. General strategies are available for making dominant negative mutants (see for example, Herskowitz, Nature (1987) 329: 219, and the references cited above). Such techniques are used to create loss of function mutations, which are useful for determining protein function. Methods that are well known to those skilled in the art can be used to construct expression vectors containing coding sequences and appropriate transcriptional and translational control signals for increased expression of an exogenous gene introduced into a cell. These methods include, for example, in vitro recombinant DNA techniques, synthetic techniques, and in vivo genetic recombination. Alternatively, RNA capable of encoding gene product sequences may be chemically synthesized using, for example, synthesizers. See, for example, the techniques described in "Oligonucleotide Synthesis", 1984, Gait, M. J. ed., IRL Press, Oxford.

In yet other embodiments, the agent is an agent that modulates, e.g., inhibits, B2M activity by binding to B2M and/or inhibiting binding of B2M to a second protein, e.g., a protein member of MHC1. For example, small molecules that bind to the B2M and inhibit its activity are of interest. Naturally occurring or synthetic small molecule compounds of interest include numerous chemical classes, such as organic molecules, e.g., small organic compounds having a molecular weight of more than 50 and less than about 2,500 daltons. Candidate agents comprise functional groups for structural interaction with proteins, particularly hydrogen bonding, and typically include at least an amine, carbonyl, hydroxyl or carboxyl group, preferably at least two of the functional chemical groups. The candidate agents may include cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Such molecules may be identified, among other ways, by employing the screening protocols described below. Specific examples of small molecule agents that may be employed to reduce B2M expression include, but are not limited to: Riamycin SV: (7S,9E,11S,12R,13S,14R,15R,16R,17S,18S,19E,21Z)-2,15,17,27,29-pentahydroxy-11-methoxy-3,7,12,14,16,18,22-heptamethyl-26-{(E)-[(4-methylpiperazin-1-yl)imino]methyl}-6,23-dioxo-8,30-dioxa-24-azatetracyclo[23.3.1.14, 7.05,28]triaconta-1(28),2,4,9,19,21,25(29),26-octaen-13-yl acetate (as disclosed in Woods, et al., "Ligand binding to distinct states diverts aggregation of an amyloid-forming protein" Nature Chemical Biology (2011) 7: 730-9); meclocycline, doxycycline, 4-epi-oxytetracylcine, rolitetracycline, anhydrochlortetracycline, methacycline and oxytetracycline (as described in Giorgetti, et al., "Effect of tetracyclines on the dynamics of formation and destructuration of beta2-microglobulin amyloid fibrils," The Journal of Biological Chemistry (2011) 286: 2121-31); peptides D-TLKIVW, D-TWKLVL, D-YVIIER and D-DYYFEF (as described in U.S. Pat. No. 8,754,034); as well as the agents described in: Morozov, et al., "Survey of small molecule and ion binding to beta 2-microglobulin—possible relation to BEN," (1991) 34: S85-8, Regazzoni, et al., "Screening of fibrillogenesis inhibitors of B2-microglobulin: integrated strategies by mass spectrometry capillary electrophoresis and in silico simulations," Analytica Chimica Acta (2011) 685: 153-61, Quaglia, et al., "Search of ligands for the amyloidogenic protein beta2-microglobulin by capillary electrophoresis and other techniques," Electrophoresis (2005) 26: 4055-63, Ozawa, et al., "Inhibition of beta2-microglobulin amyloid fibril formation by alpha2-macroglobulin," The Journal of Biological Chemistry (2011) 286: 9668-9676, Pullara and Emanuele, "Early stages of beta2-microglobulin aggregation and the inhibiting action of alphaB-crystallin," (2008)

73: 1037-46, Wanchu, et al., "Suppression of beta 2 microglobulin by pentoxiphylline therapy in asymptomatic HIV infected individuals," (2001) 113: 75-7, Brancolini, et al., "Can small hydrophobic gold nanoparticles inhibit B2-microglobulin fibrillation?," Nanoscale (2014) 6: 7903-11, US20040127445 and US20130331327.

In certain embodiments, the administered active agent is a B2M specific binding member. In general, useful B2M specific binding members exhibit an affinity (Kd) for a target B2M, such as human B2M, that is sufficient to provide for the desired reduction in aging associated impairment B2M activity. As used herein, the term "affinity" refers to the equilibrium constant for the reversible binding of two agents; "affinity" can be expressed as a dissociation constant (Kd). Affinity can be at least 1-fold greater, at least 2-fold greater, at least 3-fold greater, at least 4-fold greater, at least 5-fold greater, at least 6-fold greater, at least 7-fold greater, at least 8-fold greater, at least 9-fold greater, at least 10-fold greater, at least 20-fold greater, at least 30-fold greater, at least 40-fold greater, at least 50-fold greater, at least 60-fold greater, at least 70-fold greater, at least 80-fold greater, at least 90-fold greater, at least 100-fold greater, or at least 1000-fold greater, or more, than the affinity of an antibody for unrelated amino acid sequences. Affinity of a specific binding member to a target protein can be, for example, from about 100 nanomolar (nM) to about 0.1 nM, from about 100 nM to about 1 picomolar (pM), or from about 100 nM to about 1 femtomolar (fM) or more. The term "binding" refers to a direct association between two molecules, due to, for example, covalent, electrostatic, hydrophobic, and ionic and/or hydrogen-bond interactions, including interactions such as salt bridges and water bridges. In some embodiments, the antibodies bind human B2M with nanomolar affinity or picomolar affinity. In some embodiments, the antibodies bind human B2M with a Kd of less than about 100 nM, 50 nM, 20 nM, 20 nM, or 1 nM.

Examples of B2M specific binding members include B2M antibodies and binding fragments thereof. Non-limiting examples of such antibodies include antibodies directed against any epitope of B2M. Also encompassed are bispecific antibodies, i.e., antibodies in which each of the two binding domains recognizes a different binding epitope. The amino acid sequence of human B2M is disclosed in Cunningham, et al., "The complete amino acid sequence of beta-2-microglobulin," Biochemistry (1973) 12: 4811-4821.

Antibody specific binding members that may be employed include full antibodies or immunoglobulins of any isotype, as well as fragments of antibodies which retain specific binding to antigen, including, but not limited to, Fab, Fv, scFv, and Fd fragments, chimeric antibodies, humanized antibodies, single-chain antibodies, and fusion proteins comprising an antigen-binding portion of an antibody and a non-antibody protein. The antibodies may be detectably labeled, e.g., with a radioisotope, an enzyme which generates a detectable product, a fluorescent protein, and the like. The antibodies may be further conjugated to other moieties, such as members of specific binding pairs, e.g., biotin (member of biotin-avidin specific binding pair), and the like. Also encompassed by the term are Fab', Fv, F(ab')2, and or other antibody fragments that retain specific binding to antigen, and monoclonal antibodies. An antibody may be monovalent or bivalent.

"Antibody fragments" comprise a portion of an intact antibody, for example, the antigen binding or variable region of the intact antibody. Examples of antibody fragments include Fab, Fab', F(ab')2, and Fv fragments; diabodies; linear antibodies (Zapata et al., Protein Eng. 8(10): 1057-1062 (1995)); single-chain antibody molecules; and multispecific antibodies formed from antibody fragments. Papain digestion of antibodies produces two identical antigen-binding fragments, called "Fab" fragments, each with a single antigen-binding site, and a residual "Fc" fragment, a designation reflecting the ability to crystallize readily. Pepsin treatment yields an F(ab')2 fragment that has two antigen combining sites and is still capable of cross-linking antigen.

"Fv" is the minimum antibody fragment which contains a complete antigen-recognition and -binding site. This region consists of a dimer of one heavy- and one light-chain variable domain in tight, non-covalent association. It is in this configuration that the three CDRS of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The "Fab" fragment also contains the constant domain of the light chain and the first constant domain (CH1) of the heavy chain. Fab fragments differ from Fab' fragments by the addition of a few residues at the carboxyl terminus of the heavy chain CH1 domain including one or more cysteines from the antibody hinge region. Fab'-SH is the designation herein for Fab' in which the cysteine residue(s) of the constant domains bear a free thiol group. F(ab')2 antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa and lambda, based on the amino acid sequences of their constant domains. Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA, and IgA2.

"Single-chain Fv" or "sFv" antibody fragments comprise the VH and VL domains of antibody, wherein these domains are present in a single polypeptide chain. In some embodiments, the Fv polypeptide further comprises a polypeptide linker between the VH and VL domains, which enables the sFv to form the desired structure for antigen binding. For a review of sFv, see Pluckthun in The Pharmacology of Monoclonal Antibodies, vol. 113, Rosenburg and Moore eds., Springer-Verlag, New York, pp. 269-315 (1994).

Antibodies that may be used in connection with the present disclosure thus can encompass monoclonal antibodies, polyclonal antibodies, bispecific antibodies, Fab antibody fragments, F(ab)2 antibody fragments, Fv antibody fragments (e.g., VH or VL), single chain Fv antibody fragments and dsFv antibody fragments. Furthermore, the antibody molecules may be fully human antibodies, humanized antibodies, or chimeric antibodies. In some embodiments, the antibody molecules are monoclonal, fully human antibodies.

The antibodies that may be used in connection with the present disclosure can include any antibody variable region, mature or unprocessed, linked to any immunoglobulin constant region. If a light chain variable region is linked to a constant region, it can be a kappa chain constant region. If a heavy chain variable region is linked to a constant region, it can be a human gamma 1, gamma 2, gamma 3 or gamma 4 constant region, more preferably, gamma 1, gamma 2 or gamma 4 and even more preferably gamma 1 or gamma 4.

In some embodiments, fully human monoclonal antibodies directed against B2M are generated using transgenic mice carrying parts of the human immune system rather than the mouse system.

Minor variations in the amino acid sequences of antibodies or immunoglobulin molecules are encompassed by the present invention, providing that the variations in the amino acid sequence maintain at least 75%, e.g., at least 80%, 90%, 95%, or 99% of the sequence. In particular, conservative amino acid replacements are contemplated. Conservative replacements are those that take place within a family of amino acids that are related in their side chains. Whether an amino acid change results in a functional peptide can readily be determined by assaying the specific activity of the polypeptide derivative. Fragments (or analogs) of antibodies or immunoglobulin molecules can be readily prepared by those of ordinary skill in the art. Preferred amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known. Sequence motifs and structural conformations may be used to define structural and functional domains in accordance with the invention.

Specific examples of antibody agents that may be employed to reduce B2M expression include, but are not limited to: Anti-B2m B1-1G6 (immunoglobulin G2a [IgG2]), B2-62-2 (IgG2a), and C21-48A (IgG2b) from Immunotech S.A. (Marseille, France); Anti-B2m MAb HC11-151-1 (IgG1) (as disclosed in Corbeau, et al., "An early postinfection signal mediated by monoclonal anti-beta 2 microglobulin antibody is responsible for delayed production of human immunodeficiency virus type 1 in peripheral blood mononuclear cells," Journal of Virology (1990) 64: 1459-64); clone B2, mouse IgG1 (Sero-tec Ltd., Oxford, UK); mouse mAbs against human B2M as disclosed in Yang, et al., "Targeting beta(2)-microglobulin for induction of tumor apoptosis in human hematological malignancies," (2006) 10: 295-307; 1B749 (IgG2a) and HB28 (IgG2b) (as disclosed in Pokrass, et al., "Activation of complement by monoclonal antibodies that target cell-associated B2-microglobulin: implications for cancer immunotherapy," (2013) 56: 549-60); anti-B2-microglobulin (BBM.1 antibody) (as disclosed in Brodsky, et al., "Characterization of a monoclonal anti-beta 2-microglobulin antibody and its use in the genetic and biochemical analysis of major histocompatibility antigens," European Journal of Immunology (1979) 9: 536-45; BBM-1 (as disclosed in Korkolopoulou, "Loss of antigen-presenting molecules (MHC class I and TAP-1) in lung cancer," British Journal of Cancer (1996) 73: 148-53; 61.1G6, C23.24.2, B2.62.2, and C21.48A1 antibodies (as disclosed in Liabeuf, et al., "An antigenic determinant of human beta 2-microglobulin masked by the association with HLA heavy chains at the cell surface: analysis using monoclonal antibodies," Journal of Immunology (1981) 127: 1542-8); as well as those antibody agents described in: Zhang, et al., "Anti-B2M monoclonal antibodies kill myeloma cells via cell- and complement-mediated cytotoxicity," International Journal of Cancer (2014) 135: 1132-41, Yang, et al., "Anti beta2-microglobulin monoclonal antibodies induce apoptosis in myeloma cells by recruiting MHC class I to and excluding growth and survival cytokine receptors from lipid rafts," Blood (2007) 110: 3028-35, Josson, et al., "Inhibition of B2-microglobulin/hemochromatosis enhances radiation sensitivity by induction of iron overload in prostate cancer cells," (2013) 8: e68366, Par and Falus, "Serum beta 2-microglobulin (beta 2m) and anti-beta 2m antibody in chronic hepatitis," Acta Medica Hungarica (1986) 43:343-9, Huang, et al., "Androgen receptor survival signaling is blocked by anti-beta2-microglobulin monoclonal antibody via a MAPK/lipogenic pathway in human prostate cancer cells," The Journal of Biological Chemistry (2010) 285: 7947-56, Tam and Messner, "Differential inhibition of mitogenic responsiveness by monoclonal antibodies to beta 2-microglobulin," (1991) 133: 219-33, Domanska, et al., "Atomic structure of a nanobody-trapped domain-swapped dimer of an amyloidogenic beta2-microglobulin variant," Proc Natl Acad Sci USA. (2011) 108(4): 1314-9, Falus, et al., "Prevalence of anti-beta-2 microglobulin autoantibodies in sera of rheumatoid arthritis patients with extra-articular manifestations," Annals of the Rheumatic Diseases, (1981) 40: 409-413, Shabunina, et al., "Immunosorbent for Removal of B2-microglobulin from Human Blood Plasma," Bulletin of Experimental Biology and Medicine (2001) 132: 984-986), WO/2010/017443, U.S. Pat. No. 7,341,721, WO/1996/002278, WO/2003/079023, and WO/1990/013657.

In those embodiments where an active agent is administered to the adult mammal, the active agent(s) may be administered to the adult mammal using any convenient administration protocol capable of resulting in the desired activity. Thus, the agent can be incorporated into a variety of formulations, e.g., pharmaceutically acceptable vehicles, for therapeutic administration. More particularly, the agents of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments (e.g., skin creams), solutions, suppositories, injections, inhalants and aerosols. As such, administration of the agents can be achieved in various ways, including oral, buccal, rectal, parenteral, intraperitoneal, intradermal, transdermal, intracheal, etc., administration.

In pharmaceutical dosage forms, the agents may be administered in the form of their pharmaceutically acceptable salts, or they may also be used alone or in appropriate association, as well as in combination, with other pharmaceutically active compounds. The following methods and excipients are merely exemplary and are in no way limiting.

For oral preparations, the agents can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The agents can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The agents can be utilized in aerosol formulation to be administered via inhalation. The compounds of the present invention can be formulated into pressurized acceptable propellants such as dichlorodifluoromethane, propane, nitrogen and the like.

Furthermore, the agents can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Where the agent is a polypeptide, polynucleotide, analog or mimetic thereof, it may be introduced into tissues or host cells by any number of routes, including viral infection, microinjection, or fusion of vesicles. Jet injection may also be used for intramuscular administration, as described by Furth et al., Anal Biochem. (1992) 205:365-368. The DNA may be coated onto gold microparticles, and delivered intradermally by a particle bombardment device, or "gene gun" as described in the literature (see, for example, Tang et al., Nature (1992) 356:152-154), where gold microprojectiles are coated with the DNA, then bombarded into skin cells. For nucleic acid therapeutic agents, a number of different delivery vehicles find use, including viral and non-viral vector systems, as are known in the art.

Those of skill in the art will readily appreciate that dose levels can vary as a function of the specific compound, the nature of the delivery vehicle, and the like. Preferred dosages for a given compound are readily determinable by those of skill in the art by a variety of means.

In those embodiments where an effective amount of an active agent is administered to the adult mammal, the amount or dosage is effective when administered for a suitable period of time, such as one week or longer, including two weeks or longer, such as 3 weeks or longer, 4 weeks or longer, 8 weeks or longer, etc., so as to evidence a reduction in the impairment, e.g., cognition decline and/or cognitive improvement in the adult mammal. For example, an effective dose is the dose that, when administered for a suitable period of time, such as at least about one week, and maybe about two weeks, or more, up to a period of about 3 weeks, 4 weeks, 8 weeks, or longer, will slow e.g., by about 20% or more, e.g., by 30% or more, by 40% or more, or by 50% or more, in some instances by 60% or more, by 70% or more, by 80% or more, or by 90% or more, e.g., will halt, cognitive decline in a patient suffering from natural aging or an aging-associated disorder. In some instances, an effective amount or dose of active agent will not only slow or halt the progression of the disease condition but will also induce the reversal of the condition, i.e., will cause an improvement in cognitive ability. For example, in some instances, an effective amount is the amount that when administered for a suitable period of time, usually at least about one week, and maybe about two weeks, or more, up to a period of about 3 weeks, 4 weeks, 8 weeks, or longer will improve the cognitive abilities of an individual suffering from an aging-associated cognitive impairment by, for example 1.5-fold, 2-fold, 3-fold, 4-fold, 5-fold, in some instances 6-fold, 7-fold, 8-fold, 9-fold, or 10-fold or more relative to cognition prior to administration of the blood product.

Where desired, effectiveness of treatment may be assessed using any convenient protocol. Cognition tests and IQ test for measuring cognitive ability, e.g., attention and concentration, the ability to learn complex tasks and concepts, memory, information processing, visuospatial function, the ability to produce and understanding language, the ability to solve problems and make decisions, and the ability to perform executive functions, are well known in the art, any of which may be used to measure the cognitive ability of the individual before and/or during and after treatment with the subject blood product, e.g., to confirm that an effective amount has been administered. These include, for example, the General Practitioner Assessment of Cognition (GPCOG) test, the Memory Impairment Screen, the Mini Mental State Examination (MMSE), the California Verbal Learning Test, Second Edition, Short Form, for memory, the Delis-Kaplan Executive Functioning System test, the Alzheimer's Disease Assessment Scale (ADAS-Cog), the Psychogeriatric Assessment Scale (PAS) and the like. Progression of functional brain improvements may be detected by brain imaging techniques, such as Magnetic Resonance Imaging (MRI) or Positron Emission Tomography (PET) and the like. A wide range of additional functional assessments may be applied to monitor activities of daily living, executive functions, mobility, etc. In some embodiments, the method comprises the step of measuring cognitive ability, and detecting a decreased rate of cognitive decline, a stabilization of cognitive ability, and/or an increase in cognitive ability after administration of the blood product as compared to the cognitive ability of the individual before the blood product was administered. Such measurements may be made a week or more after administration of the blood product, e.g., 1 week, 2 weeks, 3 weeks, or more, for instance, 4 weeks, 6 weeks, or 8 weeks or more, e.g., 3 months, 4 months, 5 months, or 6 months or more.

Biochemically, by an "effective amount" or "effective dose" of active agent is meant an amount of active agent that will inhibit, antagonize, decrease, reduce, or suppress by about 20% or more, e.g., by 30% or more, by 40% or more, or by 50% or more, in some instances by 60% or more, by 70% or more, by 80% or more, or by 90% or more, in some cases by about 100%, i.e., to negligible amounts, and in some instances reverse, the reduction in synaptic plasticity and loss of synapses that occurs during the natural aging process or during the progression of an aging-associated disorder. In other words, cells present in adult mammals treated in accordance with methods of the invention will become more responsive to cues, e.g., activity cues, which promote the formation and maintenance of synapses.

Performance of methods of the invention, e.g., as described above, may manifest as improvements in observed synaptic plasticity, both in vitro and in vivo as an induction of long term potentiation. For example, the induction of LTP in neural circuits may be observed in awake individuals, e.g., by performing non-invasive stimulation techniques on awake individuals to induce LTP-like long-lasting changes in localized neural activity (Cooke S F, Bliss T V (2006) Plasticity in the human central nervous system. Brain. 129(Pt 7):1659-73); mapping plasticity and increased neural circuit activity in individuals, e.g., by using positron emission tomography, functional magnetic resonance imaging, and/or transcranial magnetic stimulation (Cramer and Bastings, "Mapping clinically relevant plasticity after stroke," Neuropharmacology (2000) 39:842-51); and by detecting neural plasticity following learning, i.e., improvements in memory, e.g., by assaying retrieval-related brain activity (Buchmann et al., "Prion protein M129V polymorphism affects retrieval-related brain activity," Neuropsychologia. (2008) 46:2389-402) or, e.g., by imaging brain tissue by functional magnetic resonance imaging (fMRI) following repetition priming with familiar and unfamiliar objects (Soldan et al., "Global familiarity of visual stimuli affects repetition-related neural plasticity but not repetition priming," Neuroimage. (2008) 39:515-26; Soldan et al., "Aging does not affect brain patterns of repetition effects associated with perceptual priming of novel objects," J. Cogn. Neurosci. (2008) 20:1762-76). In some embodiments, the method includes the step of measuring synaptic plasticity, and detecting a decreased rate of loss of synaptic plasticity, a stabilization of synaptic plasticity, and/or an increase in synaptic plasticity after administration of the blood product as compared to the synaptic plasticity of the individual before the blood product was administered. Such measurements may be made a week or more after administration of the blood product, e.g., 1 week, 2 weeks, 3 weeks, or more, for instance, 4 weeks, 6 weeks, or 8 weeks or more, e.g., 3 months, 4 months, 5 months, or 6 months or more.

In some instances, the methods result in a change in expression levels of one or more genes in one or more tissues of the host, e.g., as compared to a suitable control (such as described in the Experimental section, below). The change in expression level of a given gene may be 0.5 fold or greater, such as 1.0 fold or greater, including 1.5 fold or greater. The tissue may vary, and in some instances is nervous system tissue, e.g., central nervous system tissue, including brain tissue, e.g., hippocampal tissue. In some instances, the modulation of hippocampal gene expression is manifested as enhanced hippocampal plasticity, e.g., as compared to a suitable control.

In some instances, treatment results in an enhancement in the levels of one or more proteins in one or more tissues of the host, e.g., as compared to a suitable control (such as described in the Experimental section, below). The change in protein level of a given protein may be 0.5 fold or greater, such as 1.0 fold or greater, including 1.5 fold or greater, where in some instances the level may approach that of a healthy wild-type level, e.g., within 50% or less, such as 25% or less, including 10% or less, e.g., 5% or less of the healthy wild-type level. The tissue may vary, and in some instances is nervous system tissue, e.g., central nervous system tissue, including brain tissue, e.g., hippocampal tissue.

In some instances, the methods result in one or more structural changes in one or more tissues. The tissue may vary, and in some instances is nervous system tissue, e.g., central nervous system tissue, including brain tissue, e.g., hippocampal tissue. Structure changes of interest include an increase in dendritic spine density of mature neurons in the dentate gyrus (DG) of the hippocampus, e.g., as compared to a suitable control. In some instances, the modulation of hippocampal structure is manifested as enhanced synapse formation, e.g., as compared to a suitable control. In some instances, the methods may result in an enhancement of long term potentiation, e.g., as compared to a suitable control.

In some instances, practice of the methods, e.g., as described above, results in an increase in neurogenesis in the adult mammal. The increase may be identified in a number of different ways, e.g., as described below in the Experimental section. In some instances, the increase in neurogenesis manifests as an increase the amount of Dcx-positive immature neurons, e.g., where the increase may be 2-fold or greater. In some instances, the increase in neurogenesis manifests as an increase in the number of BrdU/NeuN positive cells, where the increase may be 2-fold or greater.

In some instances, the methods result in enhancement in learning and memory, e.g., as compared to a suitable control. Enhancement in learning and memory may be evaluated in a number of different ways, e.g., the contextual fear conditioning and/or radial arm water maze (RAWM) paradigms described in the experimental section, below. When measured by contextual fear conditioning, treatment results in some instances in increased freezing in contextual, but not cued, memory testing. When measured by RAWM, treatment results in some instances in enhanced learning and memory for platform location during the testing phase of the task. In some instances, treatment is manifested as enhanced cognitive improvement in hippocampal-dependent learning and memory, e.g., as compared to a suitable control.

In some embodiments, B2M level reduction, e.g., as described above, may be performed in conjunction with an active agent having activity suitable to treat aging-associated cognitive impairment. For example, a number of active agents have been shown to have some efficacy in treating the cognitive symptoms of Alzheimer's disease (e.g., memory loss, confusion, and problems with thinking and reasoning), e.g., cholinesterase inhibitors (e.g., Donepezil, Rivastigmine, Galantamine, Tacrine), Memantine, and Vitamin E. As another example, a number of agents have been shown to have some efficacy in treating behavioral or psychiatric symptoms of Alzheimer's Disease, e.g., citalopram (Celexa), fluoxetine (Prozac), paroxeine (Paxil), sertraline (Zoloft), trazodone (Desyrel), lorazepam (Ativan), oxazepam (Serax), aripiprazole (Abilify), clozapine (Clozaril), haloperidol (Haldol), olanzapine (Zyprexa), quetiapine (Seroquel), risperidone (Risperdal), and ziprasidone (Geodon).

In some aspects of the subject methods, the method further comprises the step of measuring cognition and/or synaptic plasticity after treatment, e.g., using the methods described herein or known in the art, and determining that the rate of cognitive decline or loss of synaptic plasticity have been reduced and/or that cognitive ability or synaptic plasticity have improved in the individual. In some such instances, the determination is made by comparing the results of the cognition or synaptic plasticity test to the results of the test performed on the same individual at an earlier time, e.g., 2 weeks earlier, 1 month earlier, 2 months earlier, 3 months earlier, 6 months earlier, 1 year earlier, 2 years earlier, 5 years earlier, or 10 years earlier, or more.

In some embodiments, the subject methods further include diagnosing an individual as having a cognitive impairment, e.g., using the methods described herein or known in the art for measuring cognition and synaptic plasticity, prior to administering the subject plasma-comprising blood product. In some instances, the diagnosing will comprise measuring cognition and/or synaptic plasticity and comparing the results of the cognition or synaptic plasticity test to one or more references, e.g., a positive control and/or a negative control. For example, the reference may be the results of the test performed by one or more age-matched individuals that experience aging-associated cognitive impairments (i.e., positive controls) or that do not experience aging-associated cognitive impairments (i.e., negative controls). As another example, the reference may be the results of the test performed by the same individual at an earlier time, e.g., 2 weeks earlier, 1 month earlier, 2 months earlier, 3 months earlier, 6 months earlier, 1 year earlier, 2 years earlier, 5 years earlier, or 10 years earlier, or more.

In some embodiments, the subject methods further comprise diagnosing an individual as having an aging-associated disorder, e.g., Alzheimer's disease, Parkinson's disease, frontotemporal dementia, progressive supranuclear palsy, Huntington's disease, amyotrophic lateral sclerosis, spinal muscular atrophy, multiple sclerosis, multi-system atrophy, glaucoma, ataxias, myotonic dystrophy, dementia, and the like. Methods for diagnosing such aging-associated disorders are well-known in the art, any of which may be used by the ordinarily skilled artisan in diagnosing the individual. In some embodiments, the subject methods further comprise both diagnosing an individual as having an aging-associated disorder and as having a cognitive impairment.

Utility

The subject methods find use in treating, including preventing, aging-associated impairments and conditions associated therewith, such as impairments in the cognitive ability of individuals. Individuals suffering from or at risk of developing an aging-associated cognitive impairments include individuals that are about 50 years old or older, e.g., 60 years old or older, 70 years old or older, 80 years old or older, 90 years old or older, and usually no older than 100 years old, i.e., between the ages of about 50 and 100, e.g., 50, 55, 60, 65, 70, 75, 80, 85, 90, 95 or about 100 years old, and are suffering from cognitive impairment associated with natural aging process, e.g., mild cognitive impairment (M.C.I.); and individuals that are about 50 years old or older, e.g., 60 years old or older, 70 years old or older, 80 years old or older, 90 years old or older, and usually no older than 100 years old, i.e., between the ages of about 50 and 90, e.g., 50, 55, 60, 65, 70, 75, 80, 85, 90, 95 or about 100 years old, that have not yet begun to show symptoms of cognitive impairment. Examples of cognitive impairments that are due to natural aging include the following:

Mild cognitive impairment (M.C.I.) is a modest disruption of cognition that manifests as problems with memory or other mental functions such as planning, following instructions, or making decisions that have worsened over time while overall mental function and daily activities are not impaired. Thus, although significant neuronal death does not typically occur, neurons in the aging brain are vulnerable to sub-lethal age-related alterations in structure, synaptic integrity, and molecular processing at the synapse, all of which impair cognitive function.

Individuals suffering from or at risk of developing an aging-associated cognitive impairment that will benefit from treatment with the subject plasma-comprising blood product, e.g., by the methods disclosed herein, also include individuals of any age that are suffering from a cognitive impairment due to an aging-associated disorder; and individuals of any age that have been diagnosed with an aging-associated disorder that is typically accompanied by cognitive impairment, where the individual has not yet begun to present with symptoms of cognitive impairment. Examples of such aging-associated disorders include the following:

Alzheimer's disease (AD). Alzheimer's disease is a progressive, inexorable loss of cognitive function associated with an excessive number of senile plaques in the cerebral cortex and subcortical gray matter, which also contains b-amyloid and neurofibrillary tangles consisting of tau protein. The common form affects persons >60 yr old, and its incidence increases as age advances. It accounts for more than 65% of the dementias in the elderly.

The cause of Alzheimer's disease is not known. The disease runs in families in about 15 to 20% of cases. The remaining, so-called sporadic cases have some genetic determinants. The disease has an autosomal dominant genetic pattern in most early-onset and some late-onset cases but a variable late-life penetrance. Environmental factors are the focus of active investigation.

In the course of the disease, synapses, and ultimately neurons are lost within the cerebral cortex, hippocampus, and subcortical structures (including selective cell loss in the nucleus basalis of Meynert), locus caeruleus, and nucleus raphae dorsalis. Cerebral glucose use and perfusion is reduced in some areas of the brain (parietal lobe and temporal cortices in early-stage disease, prefrontal cortex in late-stage disease). Neuritic or senile plaques (composed of neurites, astrocytes, and glial cells around an amyloid core) and neurofibrillary tangles (composed of paired helical filaments) play a role in the pathogenesis of Alzheimer's disease. Senile plaques and neurofibrillary tangles occur with normal aging, but they are much more prevalent in persons with Alzheimer's disease.

Parkinson's Disease. Parkinson's Disease (PD) is an idiopathic, slowly progressive, degenerative CNS disorder characterized by slow and decreased movement, muscular rigidity, resting tremor, and postural instability. Originally considered primarily a motor disorder, PD is now recognized to also affect cognition, behavior, sleep, autonomic function, and sensory function. The most common cognitive impairments include an impairment in attention and concentration, working memory, executive function, producing language, and visuospatial function.

In primary Parkinson's disease, the pigmented neurons of the substantia nigra, locus *caeruleus*, and other brain stem dopaminergic cell groups are lost. The cause is not known. The loss of substantia nigra neurons, which project to the caudate nucleus and putamen, results in depletion of the neurotransmitter dopamine in these areas. Onset is generally after age 40, with increasing incidence in older age groups.

Secondary parkinsonism results from loss of or interference with the action of dopamine in the basal ganglia due to other idiopathic degenerative diseases, drugs, or exogenous toxins. The most common cause of secondary parkinsonism is ingestion of antipsychotic drugs or reserpine, which produce parkinsonism by blocking dopamine receptors. Less common causes include carbon monoxide or manganese poisoning, hydrocephalus, structural lesions (tumors, infarcts affecting the midbrain or basal ganglia), subdural hematoma, and degenerative disorders, including striatonigral degeneration.

Frontotemporal dementia. Frontotemporal dementia (FTD) is a condition resulting from the progressive deterioration of the frontal lobe of the brain. Over time, the degeneration may advance to the temporal lobe. Second only to Alzheimer's disease (AD) in prevalence, FTD accounts for 20% of pre-senile dementia cases. Symptoms are classified into three groups based on the functions of the frontal and temporal lobes affected: Behavioural variant FTD (bvFTD), with symptoms include lethargy and aspontaneity on the one hand, and disinhibition on the other; progressive nonfluent aphasia (PNFA), in which a breakdown in speech fluency due to articulation difficulty, phonological and/or syntactic errors is observed but word comprehension is preserved; and semantic dementia (SD), in which patients remain fluent with normal phonology and syntax but have increasing difficulty with naming and word comprehension. Other cognitive symptoms common to all FTD patients include an impairment in executive function and ability to focus. Other cognitive abilities, including perception, spatial skills, memory and praxis typically remain intact. FTD can be diagnosed by observation of reveal frontal lobe and/or anterior temporal lobe atrophy in structural MRI scans.

A number of forms of FTD exist, any of which may be treated or prevented using the subject methods and compositions. For example, one form of frontotemporal dementia is Semantic Dementia (SD). SD is characterized by a loss of semantic memory in both the verbal and non-verbal domains. SD patients often present with the complaint of word-finding difficulties. Clinical signs include fluent aphasia, anomia, impaired comprehension of word meaning, and associative visual agnosia (the inability to match semantically related pictures or objects). As the disease progresses, behavioral and personality changes are often seen similar to those seen in frontotemporal dementia although cases have been described of 'pure' semantic dementia with few late behavioral symptoms. Structural MRI imaging shows a characteristic pattern of atrophy in the temporal lobes (predominantly on the left), with inferior greater than superior involvement and anterior temporal lobe atrophy greater than posterior.

As another example, another form of frontotemporal dementia is Pick's disease (PiD, also PcD). A defining characteristic of the disease is build-up of tau proteins in neurons, accumulating into silver-staining, spherical aggregations known as "Pick bodies". Symptoms include loss of speech (aphasia) and dementia. Patients with orbitofrontal dysfunction can become aggressive and socially inappropriate. They may steal or demonstrate obsessive or repetitive stereotyped behaviors. Patients with dorsomedial or dorsolateral frontal dysfunction may demonstrate a lack of concern, apathy, or decreased spontaneity. Patients can demonstrate an absence of self-monitoring, abnormal self-awareness, and an inability to appreciate meaning. Patients with gray matter loss in the bilateral posterolateral orbitofrontal cortex and right anterior insula may demonstrate changes in eating behaviors, such as a pathologic sweet tooth. Patients with more focal gray matter loss in the anterolateral orbitofrontal cortex may develop hyperphagia. While some of the symptoms can initially be alleviated, the disease progresses and patients often die within two to ten years.

Huntington's disease. Huntington's disease (HD) is a hereditary progressive neurodegenerative disorder characterized by the development of emotional, behavioral, and psychiatric abnormalities; loss of intellectual or cognitive functioning; and movement abnormalities (motor disturbances). The classic signs of HD include the development of chorea—involuntary, rapid, irregular, jerky movements that may affect the face, arms, legs, or trunk—as well as cognitive decline including the gradual loss of thought processing and acquired intellectual abilities. There may be impairment of memory, abstract thinking, and judgment; improper perceptions of time, place, or identity (disorientation); increased agitation; and personality changes (personality disintegration). Although symptoms typically become evident during the fourth or fifth decades of life, the age at onset is variable and ranges from early childhood to late adulthood (e.g., 70s or 80s).

HD is transmitted within families as an autosomal dominant trait. The disorder occurs as the result of abnormally long sequences or "repeats" of coded instructions within a gene on chromosome 4 (4p16.3). The progressive loss of nervous system function associated with HD results from loss of neurons in certain areas of the brain, including the basal ganglia and cerebral cortex.

Amyotrophic lateral sclerosis. Amyotrophic lateral sclerosis (ALS) is a rapidly progressive, invariably fatal neurological disease that attacks motor neurons. Muscular weakness and atrophy and signs of anterior horn cell dysfunction are initially noted most often in the hands and less often in the feet. The site of onset is random, and progression is asymmetric. Cramps are common and may precede weakness. Rarely, a patient survives 30 years; 50% die within 3 years of onset, 20% live 5 years, and 10% live 10 years. Diagnostic features include onset during middle or late adult life and progressive, generalized motor involvement without sensory abnormalities. Nerve conduction velocities are normal until late in the disease. Recent studies have documented the presentation of cognitive impairments as well, particularly a reduction in immediate verbal memory, visual memory, language, and executive function.

A decrease in cell body area, number of synapses and total synaptic length has been reported in even normal-appearing neurons of the ALS patients. It has been suggested that when the plasticity of the active zone reaches its limit, a continuing loss of synapses can lead to functional impairment. Promoting the formation or new synapses or preventing synapse loss may maintain neuron function in these patients.

Multiple Sclerosis. Multiple Sclerosis (MS) is characterized by various symptoms and signs of CNS dysfunction, with remissions and recurring exacerbations. The most common presenting symptoms are paresthesias in one or more extremities, in the trunk, or on one side of the face; weakness or clumsiness of a leg or hand; or visual disturbances, e.g., partial blindness and pain in one eye (retrobulbar optic neuritis), dimness of vision, or scotomas. Common cognitive impairments include impairments in memory (acquiring, retaining, and retrieving new information), attention and concentration (particularly divided attention), information processing, executive functions, visuospatial functions, and verbal fluency. Common early symptoms are ocular palsy resulting in double vision (diplopia), transient weakness of one or more extremities, slight stiffness or unusual fatigability of a limb, minor gait disturbances, difficulty with bladder control, vertigo, and mild emotional disturbances; all indicate scattered CNS involvement and often occur months or years before the disease is recognized. Excess heat may accentuate symptoms and signs.

The course is highly varied, unpredictable, and, in most patients, remittent. At first, months or years of remission may separate episodes, especially when the disease begins with retrobulbar optic neuritis. However, some patients have frequent attacks and are rapidly incapacitated; for a few the course can be rapidly progressive.

Glaucoma. Glaucoma is a common neurodegenerative disease that affects retinal ganglion cells (RGCs). Evidence supports the existence of compartmentalized degeneration programs in synapses and dendrites, including in RGCs. Recent evidence also indicates a correlation between cognitive impairment in older adults and glaucoma (Yochim B P, et al. Prevalence of cognitive impairment, depression, and anxiety symptoms among older adults with glaucoma. J Glaucoma. 2012; 21(4):250-254).

Myotonic dystrophy. Myotonic dystrophy (DM) is an autosomal dominant multisystem disorder characterized by dystrophic muscle weakness and myotonia. The molecular defect is an expanded trinucleotide (CTG) repeat in the 3' untranslated region of the myotonin-protein kinase gene on chromosome 19q. Symptoms can occur at any age, and the range of clinical severity is broad. Myotonia is prominent in the hand muscles, and ptosis is common even in mild cases. In severe cases, marked peripheral muscular weakness occurs, often with cataracts, premature balding, hatchet facies, cardiac arrhythmias, testicular atrophy, and endocrine abnormalities (e.g., diabetes mellitus). Mental retardation is common in severe congenital forms, while an aging-related decline of frontal and temporal cognitive functions, particularly language and executive functions, is observed in milder adult forms of the disorder. Severely affected persons die by their early 50s.

Dementia. Dementia describes class of disorders having symptoms affecting thinking and social abilities severely enough to interfere with daily functioning. Other instances of dementia in addition to the dementia observed in later stages of the aging-associated disorders discussed above include vascular dementia, and dementia with Lewy bodies, described below.

In vascular dementia, or "multi-infarct dementia", cognitive impairment is caused by problems in supply of blood to the brain, typically by a series of minor strokes, or sometimes, one large stroke preceded or followed by other smaller strokes. Vascular lesions can be the result of diffuse cerebrovascular disease, such as small vessel disease, or focal lesions, or both. Patients suffering from vascular dementia present with cognitive impairment, acutely or subacutely, after an acute cerebrovascular event, after which progressive cognitive decline is observed. Cognitive impairments are similar to those observed in Alzheimer's disease, including impairments in language, memory, complex visual processing, or executive function, although the related changes in the brain are not due to AD pathology but to chronic reduced blood flow in the brain, eventually resulting in dementia. Single photon emission computed tomography (SPECT) and positron emission tomography (PET) neuroimaging may be used to confirm a diagnosis of multi-infarct dementia in conjunction with evaluations involving mental status examination.

Dementia with Lewy bodies (DLB, also known under a variety of other names including Lewy body dementia, diffuse Lewy body disease, cortical Lewy body disease, and senile dementia of Lewy type) is a type of dementia characterized anatomically by the presence of Lewy bodies (clumps of alpha-synuclein and ubiquitin protein) in neurons, detectable in post mortem brain histology. Its primary feature is cognitive decline, particularly of executive functioning. Alertness and short term memory will rise and fall. Persistent or recurring visual hallucinations with vivid and detailed pictures are often an early diagnostic symptom. DLB it is often confused in its early stages with Alzheimer's disease and/or vascular dementia, although, where Alzheimer's disease usually begins quite gradually, DLB often has a rapid or acute onset. DLB symptoms also include motor symptoms similar to those of Parkinson's. DLB is distinguished from the dementia that sometimes occurs in Parkinson's disease by the time frame in which dementia symptoms appear relative to Parkinson symptoms. Parkinson's disease with dementia (PDD) would be the diagnosis when dementia onset is more than a year after the onset of Parkinson's. DLB is diagnosed when cognitive symptoms begin at the same time or within a year of Parkinson symptoms.

Progressive supranuclear palsy. Progressive supranuclear palsy (PSP) is a brain disorder that causes serious and progressive problems with control of gait and balance, along with complex eye movement and thinking problems. One of the classic signs of the disease is an inability to aim the eyes properly, which occurs because of lesions in the area of the brain that coordinates eye movements. Some individuals describe this effect as a blurring. Affected individuals often show alterations of mood and behavior, including depression and apathy as well as progressive mild dementia. The disorders long name indicates that the disease begins slowly and continues to get worse (progressive), and causes weakness (palsy) by damaging certain parts of the brain above pea-sized structures called nuclei that control eye movements (supranuclear). PSP was first described as a distinct disorder in 1964, when three scientists published a paper that distinguished the condition from Parkinson's disease. It is sometimes referred to as Steele-Richardson-Olszewski syndrome, reflecting the combined names of the scientists who defined the disorder. Although PSP gets progressively worse, no one dies from PSP itself.

Ataxia. People with ataxia have problems with coordination because parts of the nervous system that control movement and balance are affected. Ataxia may affect the fingers, hands, arms, legs, body, speech, and eye movements. The word ataxia is often used to describe a symptom of incoordination which can be associated with infections, injuries, other diseases, or degenerative changes in the central nervous system. Ataxia is also used to denote a group of specific degenerative diseases of the nervous system called the hereditary and sporadic ataxias which are the National Ataxia Foundation's primary emphases.

Multiple-system atrophy. Multiple-system atrophy (MSA) is a degenerative neurological disorder. MSA is associated with the degeneration of nerve cells in specific areas of the brain. This cell degeneration causes problems with movement, balance, and other autonomic functions of the body such as bladder control or blood-pressure regulation. The cause of MSA is unknown and no specific risk factors have been identified. Around 55% of cases occur in men, with typical age of onset in the late 50s to early 60s. MSA often presents with some of the same symptoms as Parkinson's disease. However, MSA patients generally show minimal if any response to the dopamine medications used for Parkinson's.

In some embodiments, the subject methods and compositions find use in slowing the progression of aging-associated cognitive impairment. In other words, cognitive abilities in the individual will decline more slowly following treatment by the disclosed methods than prior to or in the absence of treatment by the disclosed methods. In some such instances, the subject methods of treatment include measuring the progression of cognitive decline after treatment, and determining that the progression of cognitive decline is reduced. In some such instances, the determination is made by comparing to a reference, e.g., the rate of cognitive decline in the individual prior to treatment, e.g., as determined by measuring cognition prior at two or more time points prior to administration of the subject blood product.

The subject methods and compositions also find use in stabilizing the cognitive abilities of an individual, e.g., an individual suffering from aging-associated cognitive decline or an individual at risk of suffering from aging-associated cognitive decline. For example, the individual may demonstrate some aging-associated cognitive impairment, and progression of cognitive impairment observed prior to treatment with the disclosed methods will be halted following treatment by the disclosed methods. As another example, the individual may be at risk for developing an aging-associated cognitive decline (e.g., the individual may be aged 50 years old or older, or may have been diagnosed with an aging-associated disorder), and the cognitive abilities of the individual are substantially unchanged, i.e., no cognitive decline can be detected, following treatment by the disclosed methods as compared to prior to treatment with the disclosed methods.

The subject methods and compositions also find use in reducing cognitive impairment in an individual suffering from an aging-associated cognitive impairment. In other words, cognitive ability is improved in the individual following treatment by the subject methods. For example, the cognitive ability in the individual is increased, e.g., by 2-fold or more, 5-fold or more, 10-fold or more, 15-fold or more, 20-fold or more, 30-fold or more, or 40-fold or more, including 50-fold or more, 60-fold or more, 70-fold or more, 80-fold or more, 90-fold or more, or 100-fold or more, following treatment by the subject methods relative to the cognitive ability that is observed in the individual prior to treatment by the subject methods. In some instances, treatment by the subject methods and compositions restores the cognitive ability in the individual suffering from aging-associated cognitive decline, e.g., to their level when the individual was about 40 years old or less. In other words, cognitive impairment is abrogated.

Reagents, Devices and Kits

Also provided are reagents, devices and kits thereof for practicing one or more of the above-described methods. The subject reagents, devices and kits thereof may vary greatly. Reagents and devices of interest include those mentioned above with respect to the methods of reducing B2M levels in an adult mammal.

In addition to the above components, the subject kits will further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, portable flash drive, etc., on which the information has been recorded. Yet another means that may be present is a website address which may be used via the internet to access the information at a removed site. Any convenient means may be present in the kits.

The following examples are provided by way of illustration and not by way of limitation.

EXPERIMENTAL

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

I. Methods

A. Animal Models.

The following mouse lines were used: C57BL/6 (The Jackson Laboratory), C57BL/6 aged mice (National Institutes of Aging), $\beta$2-Microglobulin (B2M−/−) mutant mice and transporter associated with antigen processing 1 (Tap1−/−) mutant mice (The Jackson Laboratory). All studies were done in male mice. The numbers of mice used to result in statistically significant differences was calculated using standard power calculations with $\alpha$=0.05 and a power of 0.8. We used an online tool (http://www.statuiowa.edu/~rlenth/Power/index.html) to calculate power and sample size based on experience with the respective tests, variability of the assays and inter-individual differences within groups. Mice were housed under specific pathogen-free conditions under a 12 h light-dark cycle and all animal handling and use was in accordance with institutional guidelines approved by the University of California San Francisco IACUC and the VA Palo Alto Committee on Animal Research.

B. Parabiosis.

Parabiosis surgery followed previously described procedures (Villeda, S. A., et al., "The ageing systemic milieu negatively regulates neurogenesis and cognitive function," *Nature* (2011) 477: 90-94), (Villeda, S. A. et al., "Young blood reverses age-related impairments in cognitive function and synaptic plasticity in mice," *Nature medicine* (2014) 20:659-663). Mirror-image incisions at the left and right flanks were made through the skin and shorter incisions made through the abdominal wall. The peritoneal openings of the adjacent parabionts were sutured together. Elbow and knee joints from each parabiont were sutured together and the skin of each mouse was stapled (9 mm Autoclip, Clay Adams) to the skin of the adjacent parabiont. Each mouse was injected subcutaneously with Baytril antibiotic and Buprenex as directed for pain and monitored during recovery. For overall health and maintenance behavior, several recovery characteristics were analyzed at various times after surgery, including paired weights and grooming behavior.

C. Stereotaxic Injections.

Animals were placed in a stereotaxic frame and anesthetized with 2% isoflurane (2 L/min oxygen flow rate) delivered through an anesthesia nose cone. Ophthalmic eye ointment (Puralube Vet Ointment, Dechra) was applied to the cornea to prevent desiccation during surgery. The area around the incision was trimmed. Solutions were injected bilaterally into the DG of the dorsal hippocampi using the following coordinates: (from bregma) anterior=−2 mm, lateral=1.5 mm, (from skull surface) height=−2.1 mm. A 2 µl volume was injected stereotaxically over 10 minutes (injection speed: 0.20 µl/min) using a 5 µl 26s gauge Hamilton syringe. To limit reflux along the injection track, the needle was maintained in situ for 8 minutes, slowly pulled out half way and kept in position for an additional two minutes. The skin was closed using silk suture. Each mouse was injected subcutaneously with the analgesic Buprenex. Mice were single-housed and monitored during recovery.

D. B2M Administration.

Carrier free purified human β2-Microglobulin (Lee Biosolutions) was dissolved in PBS and administered systemically (100 μg/kg) via intraorbital in young (3 months) wild type animals, or stereotaxically (0.50 μl; 0.1 μg/μl) into the DG of the hippocampus in young (3 months) wild type and $Tap1^{-/-}$ mutant. For histological analysis B2M and vehicle were administered into contralateral DG of the same animal. For behavioral analysis B2M or vehicle were administered bilaterally into the DG and mice were allowed to recover for six or 30 days prior to cognitive testing.

E. BrdU Administration and Quantification.

For short term Brdu labeling 50 mg/kg of BrdU was injected intraperitoneally into mice daily either three or six days before sacrifice. For long term BrdU labeling 50 mg/kg of BrdU was injected into mice once a day for six days and animals were sacrificed 28 days after first administration. To estimate the total number of BrdU-positive cells in the brain, we performed DAB staining for BrdU on every sixth hemibrain section for a total of six sections. The number of BrdU-positive cells in the granule cell and subgranular cell layer of the DG were counted and multiplied by 12 to estimate the total number of BrdU-positive cells in the entire DG. To determine the fate of dividing cells a total of 200 BrdU-positive cells across 4-6 sections per mouse were analyzed by confocal microscopy for co-expression with NeuN and GFAP. The number of double-positive cells was expressed as a percentage of BrdU-positive cells.

F. Immunohistochemistry.

Tissue processing and immunohistochemistry was performed on free-floating sections following standard published techniques (Villeda, S. A., et al., "The ageing systemic milieu negatively regulates neurogenesis and cognitive function," *Nature* (2011) 477: 90-94). Briefly, mice were anesthetized with 400 mg/kg chloral hydrate (Sigma-Aldrich) and transcardially perfused with 0.9% saline. Brains were removed and fixed in phosphate-buffered 4% paraformaldehyde, pH 7.4, at 4° C. for 48 h before they were sunk through 30% sucrose for cryoprotection. Brains were then sectioned coronally at 40 μm with a cryomicrotome (Leica Camera, Inc.) and stored in cryoprotective medium. Primary antibodies were: goat anti-Dcx (1:500; Santa Cruz Biotechnology; sc-8066, clone: C-18), rat anti-BrdU (1:5000, Accurate Chemical and Scientific Corp.; ab6326, clone: BU1/75), mouse anti-Nestin (1:500; Millipore; MAB353; clone: rat-401) MCM2 (1:500, BD Biosciences; 610700; clone: 46/BM28), chicken anti-Tbr2 (1:500; Millipore; AB15894), mouse anti-NeuN (1:1000; Millipore; MAB377; clone: A60), rabbit anti-GFAP (1:500; DAKO; Z0334). After overnight incubation, primary antibody staining was revealed using biotinylated secondary antibodies (Vector) and the ABC kit (Vector) with Diaminobenzidine (DAB, Sigma-Aldrich) or fluorescence conjugated secondary antibodies (Life Technologies). For BrdU labeling, brain sections were pre-treated with 2N HCl at 37° C. for 30 min and washed three times with Tris-Buffered Saline with Tween (TBST) before incubation with primary antibody. For Nestin and Tbr2 labeling, brain sections were pre-treated three times with 0.1M Citrate at 95° C. for 5 min and washed three times with Tris-Buffered Saline with Tween (TBST) before incubation with primary antibody. To estimate the total number of Dcx positive cells per DG immunopositive cells in the granule cell and subgranular cell layer of the DG were counted in every sixth coronal hemibrain section through the hippocampus for a total of six sections and multiplied by 12.

G. Western Blot Analysis.

Mouse hippocampi were dissected after perfusion of animals, snap frozen and lysed in RIPA lysis buffer (500 mM Tris, pH 7.4, 150 mM NaCl, 0.5% Na deoxycholate, 1% NP40, 0.1% SDS, and complete protease inhibitors; Roche). Tissue lysates were mixed with 4× NuPage LDS loading buffer (Invitrogen) and loaded on a 4-12% SDS polyacrylamide gradient gel (Invitrogen) and subsequently transferred onto a nitrocellulose membrane. The blots were blocked in 5% milk in Tris-Buffered Saline with Tween (TBST) and incubated with rabbit anti-actin (1:5000, Sigma; A5060) and rabbit anti-B2M (1:2500, Abcam; ab75853; clone: EP2978Y). Horseradish peroxidase-conjugated secondary antibodies (1:5000, GE Healthcare; NA934) and an ECL kit (GE Healthcare/Amersham Pharmacia Biotech) were used to detect protein signals. Multiple exposures were taken to select images within the dynamic range of the film (GE Healthcare Amersham Hyperfilm™ ECL). Selected films were scanned (300 dpi) and quantified using ImageJ software (Version 1.46k). Actin bands were used for normalization.

H. Cell Culture Assays.

Mouse neural progenitor cells were isolated from C57BL/6 mice or Dcx-reporter mice (Couillard-Despres S, et al. "In vivo optical imaging of neurogenesis: watching new neurons in the intact brain." *Molecular imaging*. 2008; 7:28-34.) as previously described (Villeda, S. A., et al., "The ageing systemic milieu negatively regulates neurogenesis and cognitive function," *Nature* (2011) 477: 90-94), (Mosher K I, et al. "Neural progenitor cells regulate microglia functions and activity." *Nature neuroscience*. 2012; 15:1485-1487). Brains from postnatal animals (1 day-old) were dissected to remove olfactory bulbs, cortex, cerebellum and brainstem. After removing superficial blood vessels hippocampi were finally minced with a scalpel, digested for 30 minutes at 37° C. in DMEMB media containing 2.5 U/ml Papain (Worthington Biochemicals), 1 U/ml Dispase II (Boeringher Mannheim), and 250 U/ml DNase I (Worthington Biochemicals) and mechanically dissociated. NSC/progenitors were purified using a 65% Percoll gradient and plated on uncoated tissue culture dishes at a density of $10^5$ cells/cm$^2$. NPCs were cultured under standard conditions for 48 hours in NeuroBasal A medium supplemented with penicillin (100 U/ml), streptomycin (100 mg/ml), 2 mM L-glutamine, serum-free B27 supplement without vitamin A (Sigma-Aldrich), bFGF (20 ng/ml) and EGF (20 ng/ml). Carrier free forms of human recombinant B2M (Vendor) were dissolved in PBS and added to cell cultures under self-renewal conditions every other day following cell plating. For proliferation BrdU incorporation was measured using a cell proliferation assay system that uses a peroxidase-coupled anti-BrdU antibody together with a color substrate for detection (Fisher). For bioluminescence assays Dcx-luciferase activity was measured using a luciferase assay system (Promega). Differentiation was assessed by immunocytochemistry using mouse anti-MAP2 (1:1000, Sigma; M9942; clone: HM-2) and rabbit anti-GFAP (1:500, DAKO; Z0334) antibodies. Cytotoxicity was measured by lactate dehydrogenase (LDH) detection using a Pierce LDH Cytotoxicity Assay system (Life Technologies).

I. Contextual Fear Conditioning.

In this task, mice learned to associate the environmental context (fear conditioning chamber) with an aversive stimulus (mild foot shock; unconditioned stimulus, US) enabling testing for hippocampal-dependent contextual fear conditioning. As contextual fear conditioning is hippocampus and amygdala dependent, the mild foot shock was paired with a light and tone cue (conditioned stimulus, CS) in order to also assess amygdala-dependent cued fear conditioning. Conditioned fear was displayed as freezing behavior. Specific training parameters are as follows: tone duration is 30 seconds; level is 70 dB, 2 kHz; shock duration is 2 seconds; intensity is 0.6 mA. This intensity is not painful and can easily be tolerated but will generate an unpleasant feeling. More specifically, on day 1 each mouse was placed in a fear-conditioning chamber and allowed to explore for 2 minutes before delivery of a 30-second tone (70 dB) ending with a 2-second foot shock (0.6 mA). Two minutes later, a second CS-US pair was delivered. On day 2 each mouse was first placed in the fear-conditioning chamber containing the same exact context, but with no CS or foot shock. Freezing was analyzed for 1-3 minutes. One hour later, the mice were placed in a new context containing a different odor, cleaning solution, floor texture, chamber walls and shape. Animals were allowed to explore for 2 minutes before being re-exposed to the CS. Freezing was analyzed for 1-3 minutes. Freezing was measured using a FreezeScan video tracking system and software (Cleversys, Inc).

J. Radial Arm Water Maze.

Spatial learning and memory was assessed using the radial arm water maze (RAWM) paradigm following the protocol described by Alamed et al. Nat. Protocols (2006) 1: 1671-1679). In this task the goal arm location containing a platform remains constant throughout the training and testing phase, while the start arm is changed during each trial. On day one during the training phase, mice are trained for 15 trails, with trials alternating between a visible and hidden platform. On day two during the testing phase, mice are tested for 15 trials with a hidden platform. Entry into an incorrect arm is scored as an error, and errors are averaged over training blocks (three consecutive trials). Investigators were blinded to genotype and treatment when scoring.

K. Plasma Collection and Proteomic Analysis.

Mouse blood was collected into EDTA coated tubes via tail vein bleed, mandibular vein bleed, or intracardial bleed at time of sacrifice. EDTA plasma was generated by centrifugation at 1000 g of freshly collected blood and aliquots were stored at −80° C. until use. Human plasma and CSF samples were obtained from University of Washington School of Medicine, Veterans Affairs Northwest Network Mental Illness Research, Education, and Clinical Center, Oregon Health Science University and University of California San Diego. Subjects were chosen based on standardized inclusion and exclusion criteria as previously described (Villeda, S. A., et al., "The ageing systemic milieu negatively regulates neurogenesis and cognitive function.," Nature (2011) 477: 90-94), (Zhang, J. et al., "CSF multi-analyte profile distinguishes Alzheimer and Parkinson diseases.," American journal of clinical pathology (2008) 129: 526-529), (Li, G. et al., "Cerebrospinal fluid concentration of brain-derived neurotrophic factor and cognitive function in non-demented subjects.," PloS one (2009) 4: e5424) and outlined in Supplementary Table 1. Informed consent was obtained from human subjects according to the institutional review board guidelines at the respective centers.

TABLE 1

| Normal aging subject inclusion criteria | Normal aging subject exclusion criteria |
| --- | --- |
| Age: Subject meets age cutoffs for entry to the specific diagnostic group.<br>Informant: Presence of an informant for all subjects.<br>General health: good enough to complete study visits,<br>Body Mass Index (BMI): 18-34<br>Stable medications for 4 weeks before the visit to draw blood or CSF.<br>Permitted medications include: AChE-inhibitors, Memantine, HRT (estrogen +/− progesterone, Lupron), Thyroid hormone, Antidepressants, statins.<br>Normal basic laboratory tests: BUN, creatinine (will allow creatinine up to 1.5), B12, TSH.<br>MMSE >27/30 (exemptions if low education and control status established by detailed evaluation)<br>Memory performance on logical Memory within normal limits.<br>CDR = 0<br>Neurological exam is normal, i.e. no evidence of stroke, Parkinsonism or major abnormalities. | Vision and/or hearing too impaired (even with correction) to allow compliance with psychometric testing<br>Medical problems: unstable, poorly controlled, or severe medical problems or diseases.<br>Cancer in the past 12 months (excludes squamous CA of the skin or stage 1 prostate CA).<br>Contraindications to lumbar puncture: Bleeding disorder, use of Coumadin, heparin or similar anticoagulant, platelets <100,000; deformity or surgery affecting lumbosacral spine which is severe enough to make lumbar puncture difficult, cutaneous sepsis at lumbosacral region.<br>Neurological disorders: neurodegenerative diseases such as Alzheimer's Disease, Parkinson's Disease, CJD, FTD, PSP; stroke in past 12 months or severe enough residual effects of earlier stroke to impair neurological or cognitive function; Multiple sclerosis; epilepsy<br>Psychiatric disorders: schizophrenia, bipolar affective disorder<br>Active/uncontrolled depression: by history or GDS score<br>Drug or alcohol abuse in past 2 years<br>Exclusionary medications (in 4 weeks before visit to draw blood or CSF)<br>Neuroleptics/atypical antipsychotics<br>Anti-Parkinson's Disease medications (L-dopa, dopamine agonists)<br>CNS stimulants: modafinil, Ritalin<br>Antiepileptic drugs (exceptions for Neurontin or similar newer AEDs given for pain control)<br>Insulin treatment<br>Cortisone (oral prohibited - topical or inhaler use allowed), anti-immune drugs (e.g. methotrexate, cytoxan, IVIg, tacrolimus, cyclosporine) or antineoplastic drugs<br>Anti-HIV medications |

The plasma concentrations of cytokines and signaling molecules were measured in human and mouse plasma samples using standard antibody-based multiplex immunoassays (Luminex) by Rules Based Medicine Inc., a fee-for-service provider. All Luminex measurements where obtained in a blinded fashion. All assays were developed and validated to Clinical Laboratory Standards Institute (formerly NCCLS) guidelines based upon the principles of immunoassay as described by the manufacturers.

L. Data and Statistical Analysis.

All experiments were randomized and blinded by an independent researcher prior to pharmacological treatment or assessment of genetic mouse models. Researchers remained blinded throughout histological, biochemical and behavioral assessments. Groups were un-blinded at the end of each experiment upon statistical analysis. Data are expressed as mean±SEM. The distribution of data in each set of experiments was tested for normality using D'Agostino-Pearson omnibus test or Shapiro-Wilk test. No significant differences in variance between groups were detected using an F test. Statistical analysis was performed with Prism 5.0 software (GraphPad Software). Means between two groups were compared with two-tailed, unpaired Student's t test. Comparisons of means from multiple groups with each other or against one control group were analyzed with 1-way ANOVA followed by appropriate post-hoc tests (indicated in figure legends).

II. Results and Discussion

Aging remains the single most dominant risk factor for dementia-related neurodegenerative diseases, such as Alzheimer's disease (Hedden & Gabrieli, "Insights into the ageing mind: a view from cognitive neuroscience," Nature reviews. Neuroscience (2004) 5:87-96; Mattson & Magnus, "Ageing and neuronal vulnerability," Nature reviews. Neuroscience (2006) 7:278-294; Small et al., "A pathophysiological framework of hippocampal dysfunction in ageing and disease," Nature reviews. Neuroscience (2011) 12:585-601). As such, it is imperative to gain mechanistic insight into what drives aging phenotypes in the brain in order to maintain cognitive integrity in the elderly, and consequently counteract vulnerability to neurodegenerative disease. We, and others, have recently shown that systemic manipulations such as heterochronic parabiosis (in which the circulatory system of a young and old animal are joined) or young plasma administration can partially reverse age-related loss of cognitive and regenerative faculties in the aged brain (Katsimpardi et al., "Vascular and neurogenic rejuvenation of the aging mouse brain by young systemic factors.," Science (2014) 344:630-634; Villeda et al., "The ageing systemic milieu negatively regulates neurogenesis and cognitive function.," Nature (2011) 477:90-94; Villeda et al., "Young blood reverses age-related impairments in cognitive function and synaptic plasticity in mice," Nature medicine (2014) 20:659-663). Interestingly, heterochronic parabiosis studies have revealed an age-dependent bi-directionality in the influence of the systemic environment indicating pro-youthful factors in young blood elicit rejuvenation while pro-aging factors in old blood drive aging (Katsimpardi et al., "Vascular and neurogenic rejuvenation of the aging mouse brain by young systemic factors.," Science (2014) 344:630-634; Villeda et al., "The ageing systemic milieu negatively regulates neurogenesis and cognitive function.," Nature (2011) 477: 90-94; Ruckh et al., "Rejuvenation of regeneration in the aging central nervous system," Cell stem cell (2012) 10:96-103; Conboy et al., "Rejuvenation of aged progenitor cells by exposure to a young systemic environment," Nature (2005) 433:760-764; Brack et al., "Increased Wnt signaling during aging alters muscle stem cell fate and increases fibrosis.," Science (2007) 317: 807-810). It has been proposed that mitigating the effect of pro-aging factors may also provide an effective approach to rejuvenate aging phenotypes (Villeda et al., "Young blood reverses age-related impairments in cognitive function and synaptic plasticity in mice," Nature medicine (2014) 20:659-663; Laviano, "Young blood," The New England journal of medicine (2014) 371:573-575; Bouchard & Villeda, "Aging and brain rejuvenation as systemic events.," Journal of neurochemistry (2014)).

In its traditional role, B2M represents the light chain of the MHC I molecules that form an active part of the adaptive immune system (Zijlstra et al., "Beta 2-microglobulin deficient mice lack CD4-8+ cytolytic T cells.," Nature (1990) 344:742-746). In the central nervous system (CNS), B2M and MHC I can act independent of their canonical immune function to regulate normal brain development, synaptic plasticity and even behavior (Lee et al. Synapse elimination and learning rules co-regulated by MHC class I H2-Db. Nature (2014) 509:195-200; Loconto et al., "Functional expression of murine V2R pheromone receptors involves selective association with the M10 and M1 families of MHC class Ib molecules.," Cell (2003) 112:607-618; Boulanger & Shatz, "Immune signalling in neural development, synaptic plasticity and disease," Nature reviews. Neuroscience (2004) 5: 521-531; Shatz, "MHC class I: an unexpected role in neuronal plasticity," Neuron (2009) 64:40-45; Huh et al., "Functional requirement for class I MHC in CNS development and plasticity," Science (2000) 290:2155-2159; Goddard et al., "Regulation of CNS synapses by neuronal MHC class I," Proceedings of the National Academy of Sciences of the United States of America (2007) 104:6828-6833; Glynn et al., "MHCI negatively regulates synapse density during the establishment of cortical connections.," Nature neuroscience (2011) 14:442-451). Additionally, in its soluble form, B2M accumulates in the systemic blood circulation as a result of cell surface shedding. Interestingly increased systemic levels of B2M have been implicated in cognitive impairments associated with chronic hemodialysis (Murray, "Cognitive impairment in the aging dialysis and chronic kidney disease populations: an occult burden," Advances in chronic kidney disease (2008) 15:123-132; Corlin et al., "Quantification of cleaved beta2-microglobulin in serum from patients undergoing chronic hemodialysis.," Clinical chemistry (2005) 51:1177-1184). Moreover, increase in soluble B2M has also been observed in the cerebral spinal fluid (CSF) of patients with HIV-dementia (McArthur et al., "The diagnostic utility of elevation in cerebrospinal fluid beta 2-microglobulin in HIV-1 dementia. Multicenter AIDS Cohort Study," Neurology (1992) 42:1707-1712; Brew et al., "Predictive markers of AIDS dementia complex: CD4 cell count and cerebrospinal fluid concentrations of beta 2-microglobulin and neopterin," The Journal of infectious diseases (1996) 174:294-298) and Alzheimer's disease (Carrette et al., "A panel of cerebrospinal fluid potential biomarkers for the diagnosis of Alzheimer's disease," Proteomics (2003) 3:1486-1494), further implicating B2M in cognitive dysfunction.

We first characterized changes in systemic levels of B2M in mouse plasma during normal aging (FIG. 1A,B), and in the experimental aging model of heterochronic parabiosis (FIG. 1C,D). We observed a three-fold increase in B2M levels in plasma derived from aged compared to young animals (FIG. 1B), and detected a corresponding increase in B2M levels in plasma derived from young heterochronic parabionts after exposure to aged blood compared to young isochronic parabionts (FIG. 1D). To corroborate systemic changes observed for B2M in aging mice with systemic changes occurring in humans, we measured B2M in archived plasma and CSF samples from healthy individuals between 20 and 90 years of age (Table 1, above). We detected an age-related increase in B2M measured in both plasma and CSF, consistent with changes observed in aging mice (FIG. 1E,F).

Figure 3:
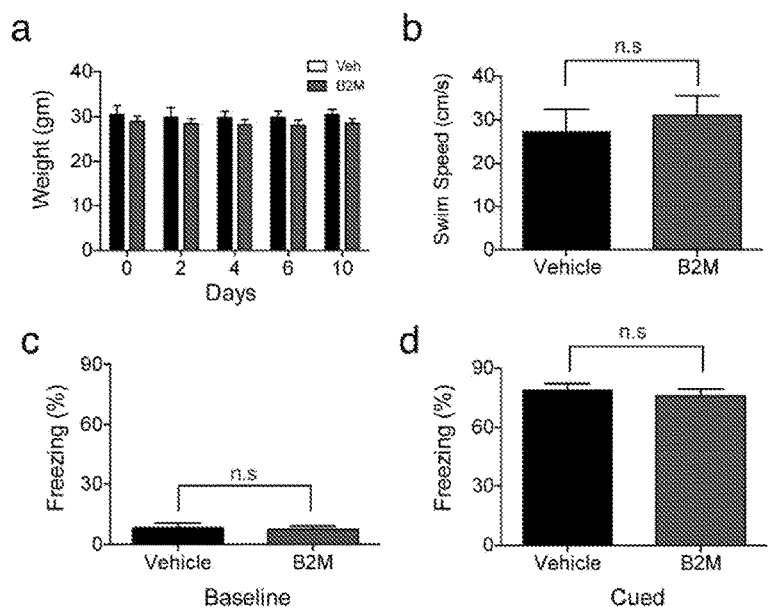
FIGS. 3a-3d. Weight, swim speeds and cued memory are not altered by systemic B2M administration.

Having identified B2M as a potential pro-aging systemic factor we next asked whether increasing B2M systemically could elicit cognitive impairments reminiscent of age-related dysfunction. As a control, we first tested hippocampal-dependent learning and memory using radial arm water maze (RAWM) and contextual fear conditioning paradigms in a cohort of young and old untreated animals and observed age-related cognitive impairments with both behavioral paradigms (FIG. 2A-E). Subsequently, we cognitively tested young adult mice systemically administered soluble B2M protein or vehicle through intraorbital injections (FIG. 1G). Animals showed no signs of illness or weight loss regardless of treatment (FIG. 3A). During the training phase of the RAWM task all mice showed similar swim speeds (FIG. 3B) and learning capacity for the task (FIG. 1H). However, during the testing phase animals receiving B2M exhibited impaired learning and memory deficits, committing significantly more errors in locating the target platform than animals receiving vehicle control (FIG. 1H). During fear conditioning training all mice, regardless of treatment, exhibited no differences in baseline freezing time (FIG. 3C). However, mice receiving B2M demonstrated decreased freezing time during contextual (FIG. 1I), but not cued (FIG. 3D), memory testing compared to vehicle treated control animals. Together, these behavioral data demonstrate that systemic administration of exogenous B2M can impair learning and memory.

Figure 4:
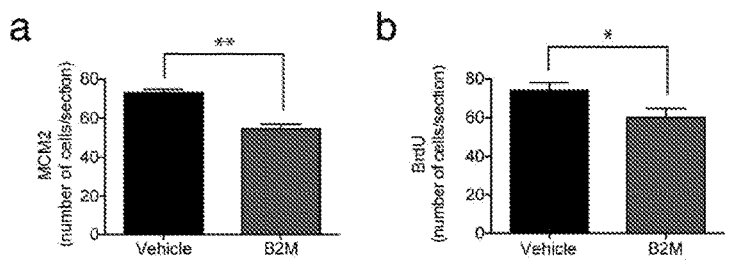
FIGS. 4a & 4b. Systemic administration of B2M decreases neurogenesis in the DG of young animals.

Impairments in hippocampal-dependent learning and memory have been previously linked with decreased adult neurogenesis (Clelland et al., "A functional role for adult hippocampal neurogenesis in spatial pattern separation," Science (2009) 325:210-213; Kitamura et al., "Adult neurogenesis modulates the hippocampus-dependent period of associative fear memory," Cell (2009) 139:814-827; Zhang et al., "A role for adult TLX-positive neural stem cells in learning and behaviour," Nature (2008) 451:1004-1007). While a causal link between age-related cognitive decline and decreased adult neurogenesis remains obfuscated (Drapeau et al., "Spatial memory performances of aged rats in the water maze predict levels of hippocampal neurogenesis.," Proceedings of the National Academy of Sciences of the United States of America (2003) 100:14385-14390; Merrill et al., "Hippocampal cell genesis does not correlate with spatial learning ability in aged rats.," The Journal of comparative neurology (2003) 459:201-207; Bizon & Gallagher, "Production of new cells in the rat dentate gyrus over the lifespan: relation to cognitive decline," The European journal of neuroscience (2003) 18:215-219; Seib et al. "Loss of Dickkopf-1 restores neurogenesis in old age and counteracts cognitive decline," Cell stem cell (2013) 12:204-214), recent studies using heterochronic parabiosis indicate that cognitive changes elicited by blood are associated with corresponding changes in adult neurogenesis (Katsimpardi et al., "Vascular and neurogenic rejuvenation of the aging mouse brain by young systemic factors," Science (2014) 344:630-634; Villeda et al., "The ageing systemic milieu negatively regulates neurogenesis and cognitive function.," Nature (2011) 477: 90-94). Consequently, we investigated whether decreased levels of adult hippocampal neurogenesis also accompanied cognitive impairments elicited by increased systemic exposure to B2M. Using immunohistochemical analysis we detected a significant decrease in the number of Doublecortin (Dcx)-positive newly born neurons (FIG. 1J,K), and Mcm2-positive progenitors (FIG. 4A) in the DG of mice systemically administrated exogenous B2M compared to mice injected with vehicle control. Consistent with changes in neurogenesis we detected a decrease in the number of proliferating cells having incorporated Bromodeoxyuridne (BrdU) in animals injected with B2M compared to vehicle (FIG. 4B). These data indicate that systemic exposure to exogenous B2M is sufficient to decrease adult neurogenesis.

Figure 5:
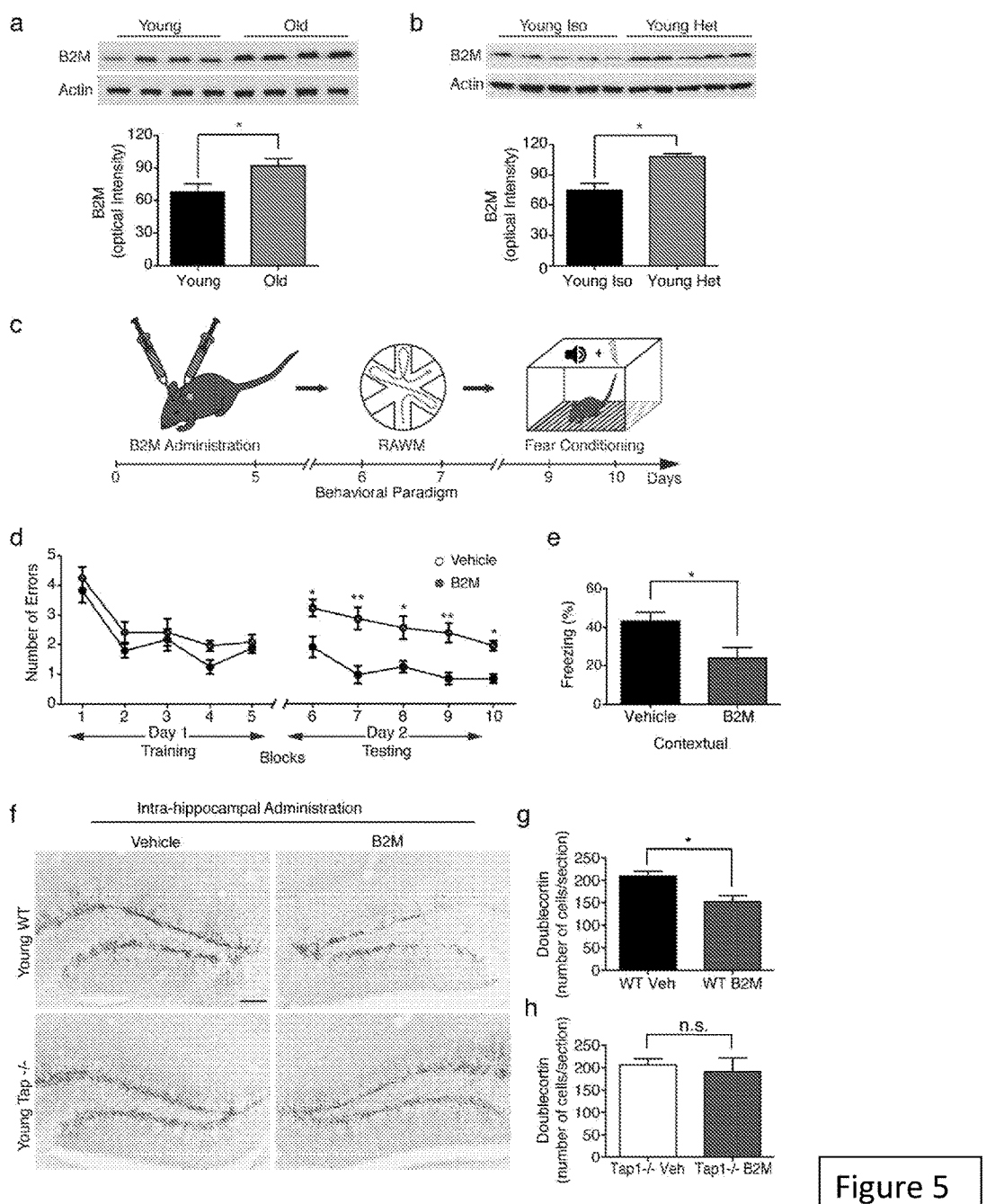
FIGS. 5a-5h. Local B2M expression increases in the hippocampus during aging and impairs hippocampal-dependent cognitive function and adult neurogenesis.

To determine whether systemic age-related changes in B2M levels were also accompanied by local changes within the brain, we measured B2M levels within the hippocampus of young and aged animals by Western blot analysis and detected an age-related increase in B2M protein (FIG. 5A). Subsequently, we asked whether systemic changes in the levels of B2M, elicited by heterochronic parabiosis, were also associated with corresponding local changes within the young hippocampus after exposure to an old systemic environment. We detected an increase in B2M protein expression in the hippocampal lysates of young heterochronic parabionts compared to young isochronic controls (FIG. 5B). Together, these data show that age-related changes in B2M observed in the systemic environment are accompanied by corresponding changes within the brain.

Figure 6:
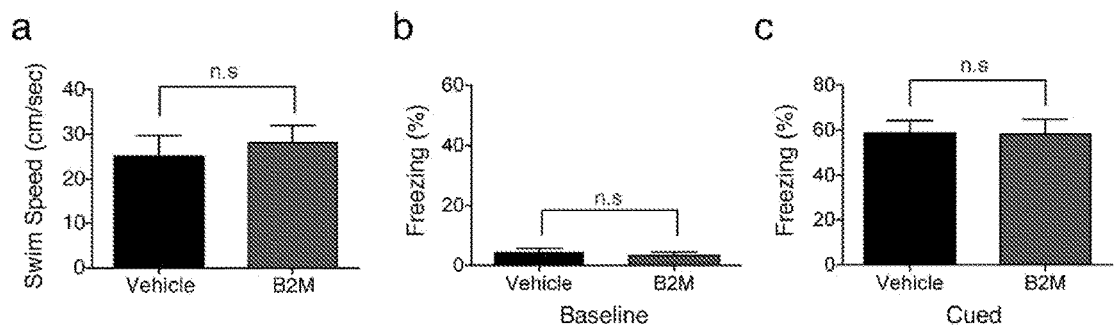
FIGS. 6a-6c. Swim speeds and cued memory are not altered by local B2M administration.

To test the effect of local exposure to exogenous B2M on learning and memory we administered B2M or vehicle control by bilateral stereotaxic injections followed by cognitive testing using RAWM and contextual fear conditioning (FIG. 5C). All mice showed similar swim speeds (FIG. 6A) and learning capacity (FIG. 5D) during the training phase of the RAWM. During the testing phase animals receiving B2M committed significantly more errors in locating the target platform than animals receiving vehicle control (FIG. 5D). During fear conditioning training no mice exhibited differences in baseline freezing time (FIG. 6B). However, mice receiving B2M demonstrated decreased freezing time during contextual (FIG. 5E), but not cued (FIG. 6C), memory testing. These functional data indicate that local exposure to B2M in the DG impairs learning and memory.

Figure 7:
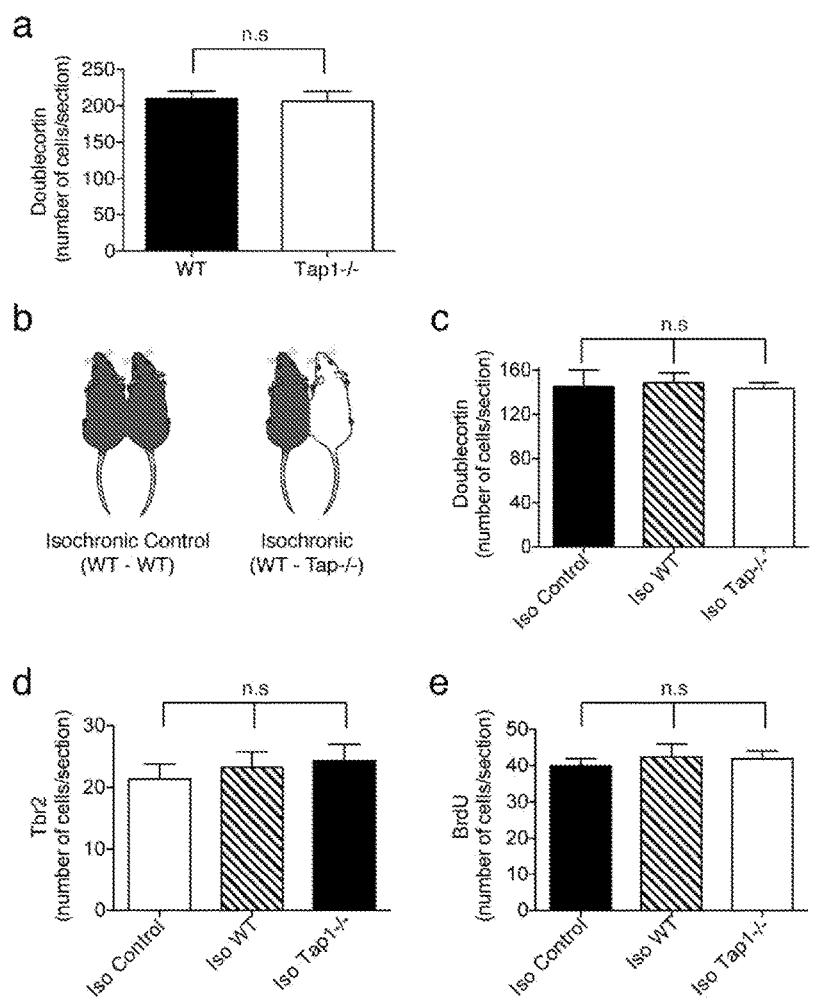
FIGS. 7a-7e. No differences in neurogenesis are observed in the DG of young unpaired or young isochronic WT and Tap1−/− animals.

To examine the effect of local exposure to exogenous B2M in the brain, we stereotaxically injected B2M into the right DG and vehicle control into the left contralateral DG of young adult mice. Local exposure of the DG to B2M resulted in a decrease in the number of Dcx-positive cells compared with the contralateral DG treated with vehicle control (FIG. 5F,G). Given B2M is an active component of the MHC I complex through non-covalent interactions on the cell surface, we next investigated whether the inhibitory effect of exogenous B2M on adult neurogenesis was mediated by MHC I cell surface expression. The transporter associated with antigen processing 1 (Tap1) protein is required for transport of MHC I molecules to the cell surface, and absence of Tap1 results in very few classical MHC I molecules reaching the cell surface (Boulanger & Shatz, "Immune signalling in neural development, synaptic plasticity and disease," Nature reviews. Neuroscience (2004) 5:521-531; Shatz, "MHC class I: an unexpected role in neuronal plasticity," Neuron (2009) 64:40-45; Van Kaer et al., "TAP1 mutant mice are deficient in antigen presentation, surface class I molecules, and CD4-8+ T cells.," Cell (1992) 71:1205-1214). Therefore, to test whether decreased surface MHC I expression could mitigate the inhibitory effect of exogenous B2M, we stereotaxically injected young adult Tap1 knock out mice (Tap1−/−) with B2M into the right DG and vehicle control into the left contralateral DG. No difference in the number of Dcx-positive cells was detected between the B2M treated DG compared to the control treated DG of TAP1−/− mice (FIG. 5F,H). Consistent with previous reports (Laguna Goya et al., "Adult neurogenesis is unaffected by a functional knock-out of MHC class I in mice," Neuroreport (2010) 21:349-353), we observed no differences in baseline levels of neurogenesis between young adult Tap1−/− and wild type (WT) littermates (FIG. 7A). Together, these data suggest that increased local levels of exogenous B2M is sufficient to decrease adult neurogenesis in a classical MHC I dependent manner.

Figure 8:
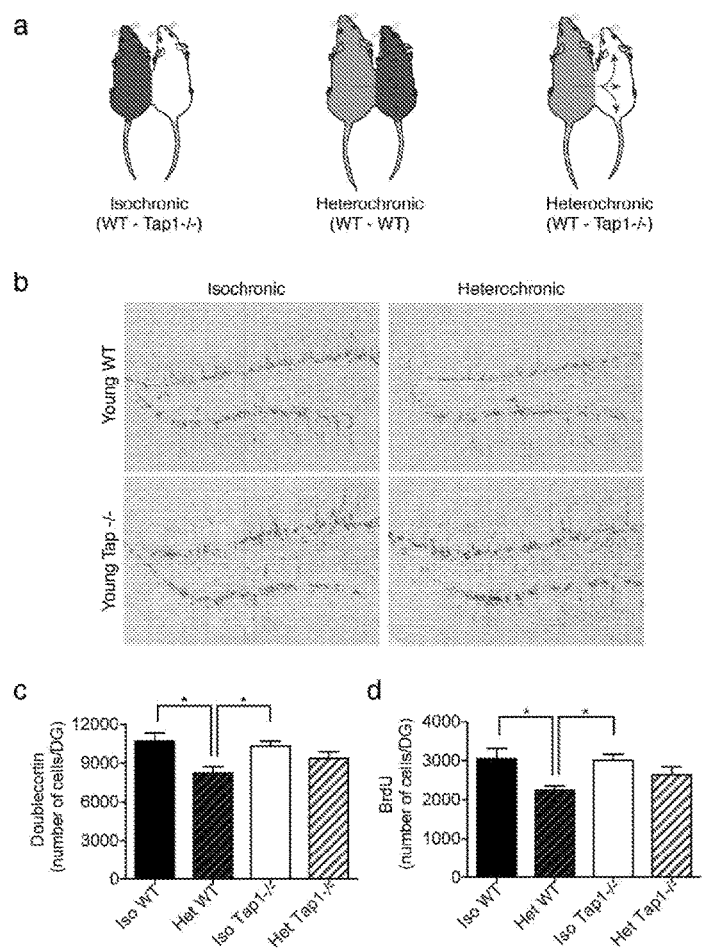
FIGS. 8a-8d. Reducing endogenous MHC I surface expression mitigates in part the negative effects of heterochronic parabiosis on adult neurogenesis in young animals.
Figure 9:
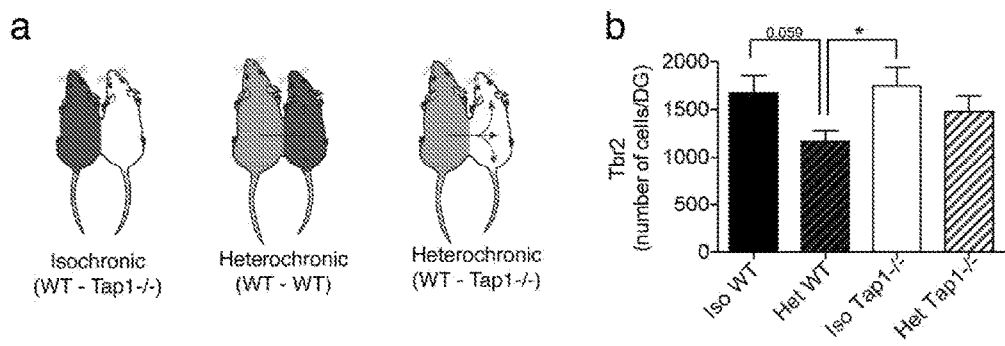
FIGS. 9a & 9b. Reducing endogenous MHC I surface expression mitigates in part the decrease in neuronal progenitor cell number in young mice after heterochronic parabiosis.

Next, we sought to investigate whether decreasing surface MHC I expression could also mitigate in part the negative effects of aged blood on adult neurogenesis elicited by heterochronic parabiosis (FIG. 8A). Consistent with previous reports (Katsimpardi et al., "Vascular and neurogenic rejuvenation of the aging mouse brain by young systemic factors.," Science (2014) 344:630-634; Villeda et al., "The ageing systemic milieu negatively regulates neurogenesis and cognitive function.," Nature (2011) 477: 90-94), we observed a decrease in the number of Dcx-positive immature neurons (FIG. 8B,C), Tbr2-positive progenitors (FIG. 9A,B), and BrdU-positive proliferating cells (FIG. 8D) in young wild type heterochronic compared to young wild type isochronic parabionts. In contrast, we did not detect robust changes in the levels of neurogenesis in young Tap1−/− heterochronic parabionts (FIG. 8B-D). As a control, no changes in neurogenesis were detected between young wild type and young Tap1−/− isochronic parabionts (FIG. 7B-D). Together, our data further substantiate the role of pro-aging factors as drivers of regenerative impairment in the adult brain, and furthermore implicate MHC I molecules in this process.

Figure 10:
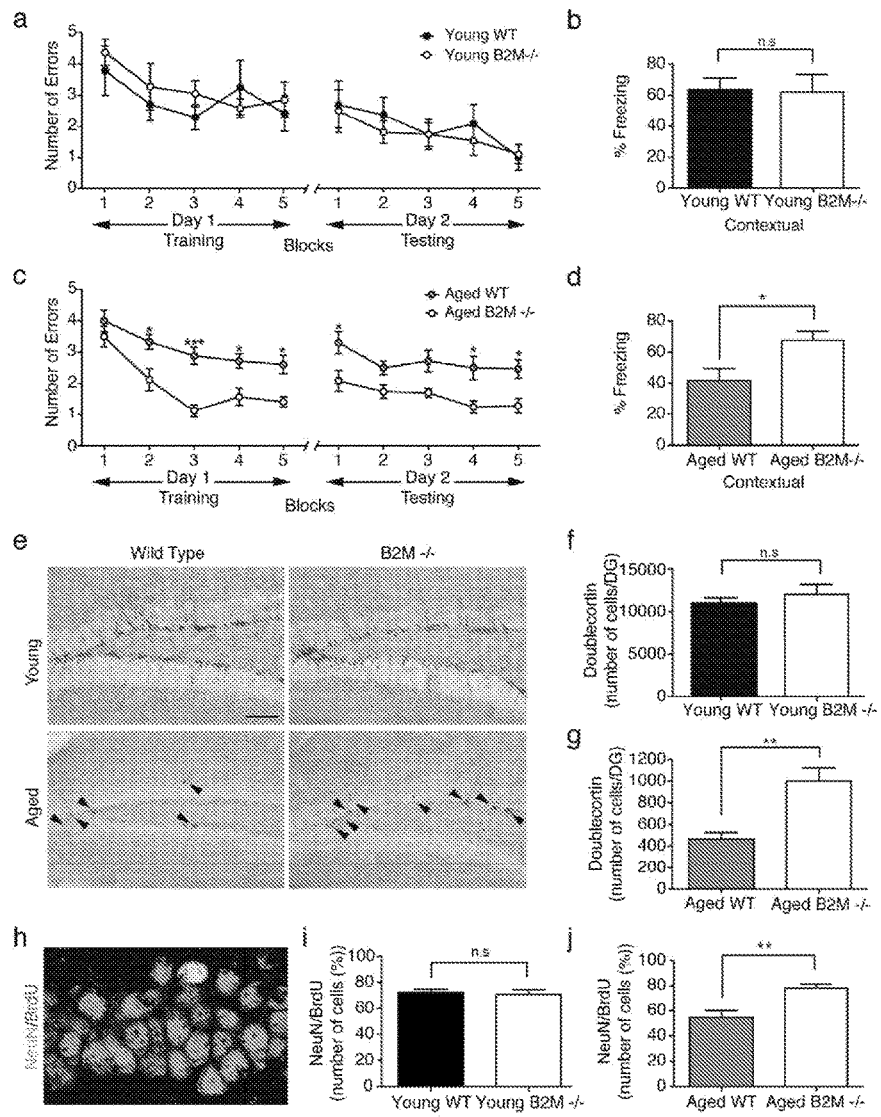
FIGS. 10a-10j. Absence of endogenous B2M enhances hippocampal-dependent cognitive function and adult neurogenesis in old animals.
Figure 11:
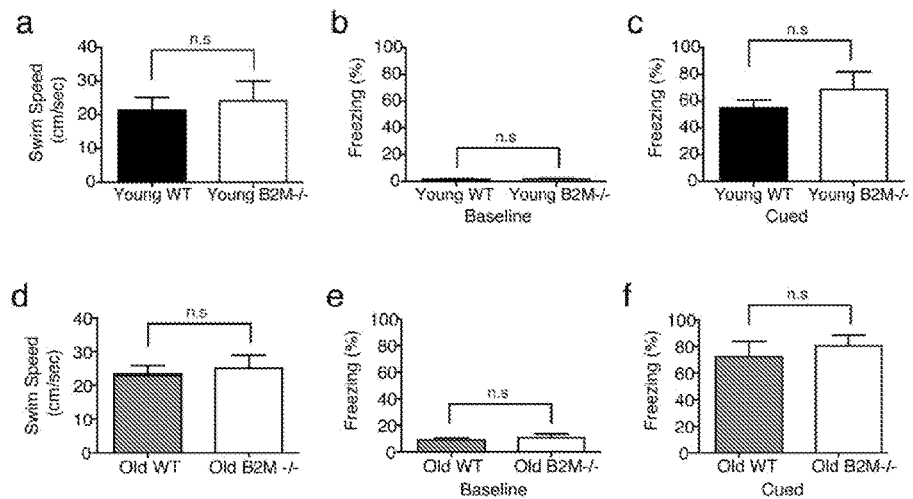
FIGS. 11a-11f. Swim speeds and cued memory are not altered in old B2M−/− animals.

Lastly, we investigated the potential benefit abrogating endogenous B2M expression could have on the age-related cognitive decline observed during aging. We utilized B2M knockout mice (B2M−/−), which lack protein expression both in the systemic environment and locally within the brain. We assessed hippocampal-dependent learning and memory in young and aged B2M−/− and WT controls using RAWM and contextual fear conditioning. In young animals no difference in spatial learning and memory were observed between B2M−/− and WT controls during RAWM training or testing (FIG. 10A). Interestingly, aged B2M−/− mice showed enhanced spatial learning capacity during the training phase of the RAWM paradigm, as well as enhanced learning and memory for platform location during the testing phase of the task compared to WT controls (FIG. 10C). Animals in each age group showed no differences in swim speed regardless of genotype (FIG. 11A,D). During fear conditioning training, all mice exhibited similar baseline freezing independent of genotype (FIG. 11B,E). Additionally, no difference in freezing was observed in young B2M−/− and WT mice during either contextual (FIG. 10B) or cued fear conditioning (FIG. 11C) paradigms. However, aged B2M−/− mice demonstrated significantly increased freezing in contextual (FIG. 10D), but not cued (FIG. 11F) memory testing compared to WT controls. Our data indicate absence of endogenous B2M ameliorates age-related impairments in hippocampal-dependent learning and memory in old animals further implicating B2M as a pro-aging factor mediating cognitive decline during aging.

Figure 12:
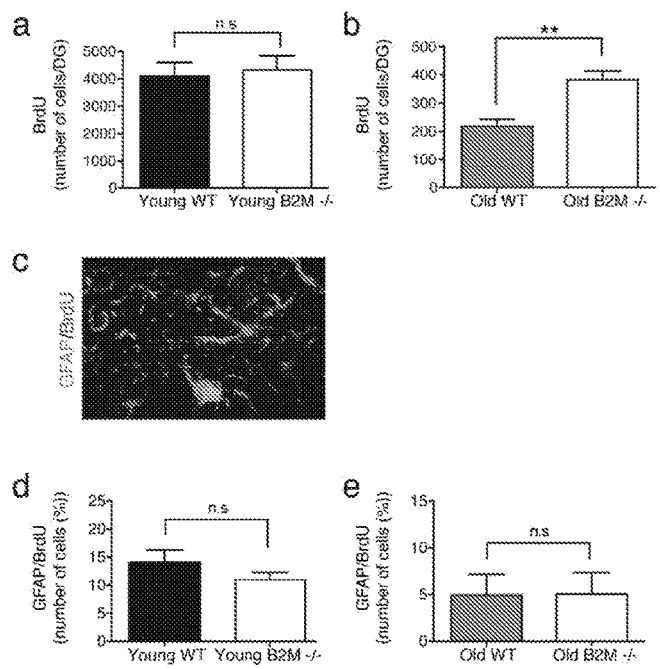
FIGS. 12a-12e. Absence of endogenous B2M increases proliferation but not astrocyte differentiation in an age-dependent manner in vivo.

Subsequently, we investigated whether absence of endogenous B2M could also counteract age-related decline in adult neurogenesis. We examined changes in neurogenesis in young and aged adult B2M−/− and WT littermates by immunohistochemical analysis. We observed that in young adult animals the absence of endogenous B2M expression had no effect on the number of Dcx-positive cells (FIG. 10E,F). Importantly, in aged animals we observed an almost 2-fold increase in the number of Dcx-positive newly born neurons in B2M−/− mice compared to wild type littermates (FIG. 10E,G). Consistent with our Dcx data, we did not detect changes in proliferation by BrdU labeling in young animals regardless of B2M expression (FIG. 12A). However, aged B2M−/− animals showed a significant increase in the number of BrdU-positive cells compared to WT controls (FIG. 12B). Subsequently, we assessed neuronal differentiation and survival in B2M−/− mice using a long-term BrdU incorporation paradigm, in which mature differentiated neurons express both BrdU and the neuronal marker NeuN (FIG. 10H). Young adult B2M−/− mice showed no differences in the percentage of cells expressing both BrdU and NeuN compared to their WT counterparts (FIG. 10I); while aged adult B2M−/− mice showed a significant increase in the percentage of cells expressing both BrdU and NeuN compared to age matched WT littermates (FIG. 10J). We detected no differences in astrocyte differentiation at any age quantified as the percentage of cells expressing BrdU and GFAP markers (FIG. 12C-E). Together, these data indicate that loss of endogenous B2M enhances the levels of neurogenesis in the aged brain, but not the young brain, indicating an active role for B2M in the decline in regenerative capacity during aging.

B2M in concert with MHC I molecules continue to be demonstrated to have a unique involvement in the CNS (Lee et al., "Synapse elimination and learning rules co-regulated by MHC class I H2-Db," Nature (2014) 509:195-200; Boulanger & Shatz, "Immune signalling in neural development, synaptic plasticity and disease," Nature reviews. Neuroscience (2004) 5:521-531; Shatz, "MHC class I: an unexpected role in neuronal plasticity," Neuron (2009) 64:40-45; Huh et al., "Functional requirement for class I MHC in CNS development and plasticity," Science (2000) 290:2155-2159; Goddard et al., "Regulation of CNS synapses by neuronal MHC class I," Proceedings of the National Academy of Sciences of the United States of America (2007) 104:6828-6833; Glynn et al., "MHCI negatively regulates synapse density during the establishment of cortical connections.," Nature neuroscience (2011) 14:442-451), with recent studies beginning to explore the curative effect of abrogating MHC I expression in brain injury models such as stroke (Adelson et al., "Neuroprotection from stroke in the absence of MHCI or PirB," Neuron (2012) 73:1100-1107). However, the functional involvement of these molecules during aging in either the CNS or peripheral tissues had not yet been investigated. Our study thus elucidates a previously unrecognized role for B2M in the progression of age-related impairments in both cognitive and regenerative processes. Moreover, our study also implicates MHC I surface expression in mediating, in part, the negative effects of B2M and heterochronic parabiosis on regenerative function. Notably, human Genome-Wide Association studies (GWAS) have linked the MHC locus on chromosome 6p21 with degenerative diseases of aging, suggesting an active role for these molecules in age-dependent impairments (Jeck et al., "Review: a meta-analysis of GWAS and age-associated diseases.," Aging cell (2012) 11:727-731). Our data now provide functional evidence for such an involvement in aging phenotypes. Our data provide mechanistic insight into how aging-related changes in the systemic environment drive impairments locally in the aged brain, and highlight the involvement of B2M and MHC I molecules in this process. From a translational perspective, our data show that age-related cognitive and regenerative dysfunction observed during aging could be ameliorated by targeting B2M at old age.

III. Determination of Relative Levels of B2M

Figure 13:
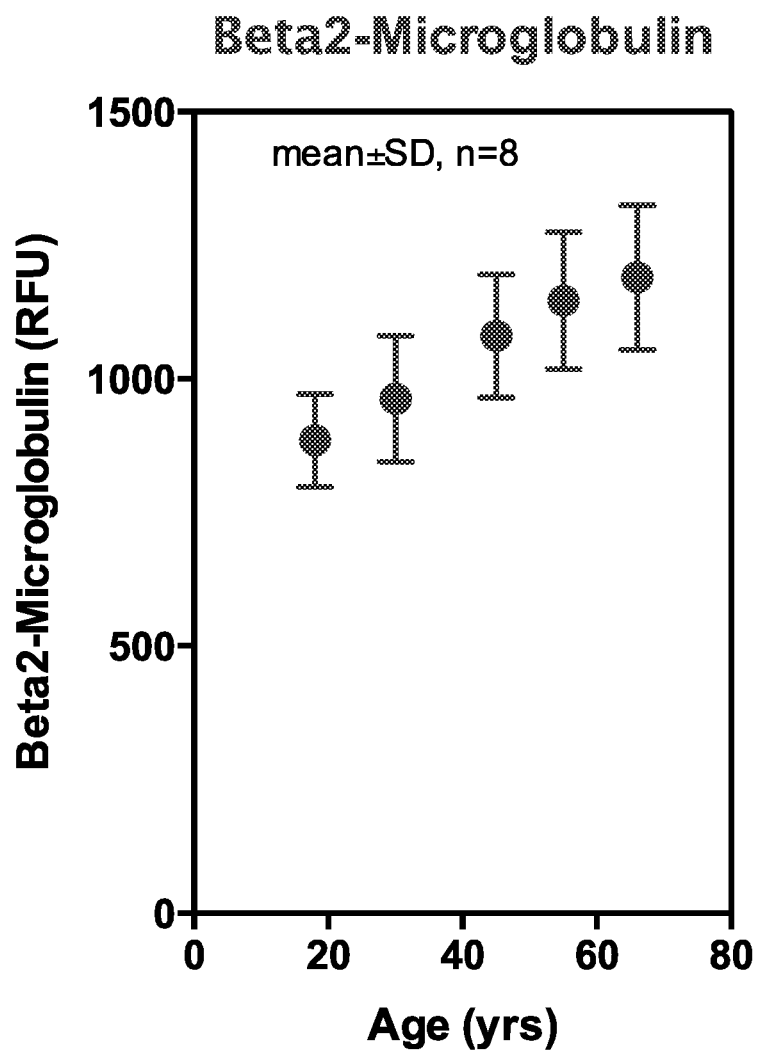
FIG. 13. Relative levels of beta2-microglobulin were determined in plasma samples of healthy male human donors of 18, 30, 45, 55, and 66 years of age by the SomaScan Proteomic Assay (Somalogic, Inc, Boulder, Colo.). For each age group, plasma from 40 individuals was analyzed as 8 pools of 5 individuals per pool. Statistical analysis was performed by two-sided Student's t-test of log-transformed values, and also by trend-analysis of untransformed data using the Jonckheere-Terpstra test. Observed changes were found to be highly significant with the p-value of the t-test being $1.1 \times 10^{-4}$ (66 vs 18 year old) and the p-value for the JT-test being $1.3 \times 10^{-7}$ (all age groups). (RFU refers to "relative fluorescence units" by SomaScan Proteomic Assay.)

Relative levels of beta2-microglobulin were determined in plasma samples of healthy male human donors of 18, 30, 45, 55, and 66 years of age by the SomaScan Proteomic Assay (Somalogic, Inc, Boulder, Colo.). For each age group, plasma from 40 individuals was analyzed as 8 pools of 5 individuals per pool. Statistical analysis was performed by two-sided Student's t-test of log-transformed values, and also by trend-analysis of untransformed data using the Jonckheere-Terpstra test. Observed changes were found to be highly significant with the p-value of the t-test being $1.1 \times 10^{-4}$ (66 vs 18 year old) and the p-value for the JT-test being $1.3 \times 10^{-7}$ (all age groups). (RFU refers to "relative fluorescence units" by SomaScan Proteomic Assay.) The results are graphically illustrated in FIG. 13.

Notwithstanding the appended clauses, the disclosure is also defined by the following clauses:

1. A method of treating an adult mammal for an aging-associated impairment, the method comprising:
reducing the β2-microglobulin (B2M) level in the mammal in a manner sufficient to treat the adult mammal for the aging-associated impairment.
2. The method according to Clause 1, wherein the method comprises reducing systemic B2M of the mammal.
3. The method according to Clause 2, wherein systemic B2M of the mammal is reduced by removing B2M from blood of the mammal.
4. The method according to Clause 3, wherein the method comprises extra-corporally removing B2M from blood of the mammal.
5. The method according to Clause 1, wherein the B2M level is reduced by administering to the mammal an effective amount of a B2M level reducing agent.
6. The method according to Clause 5, wherein the B2M level reducing agent is a B2M binding agent.
7. The method according to Clause 6, wherein the B2M binding agent comprises an antibody or binding fragment thereof.
8. The method according to Clause 6, wherein the B2M binding agent comprises a small molecule.
9. The method according to Clause 5, wherein the B2M level reducing agent comprises a B2M expression inhibitor agent.
10. The method according to Clause 9, wherein the B2M expression inhibitory agent comprises a nucleic acid.
11. The method according to any of the preceding clauses, wherein the mammal is a primate.
12. The method according to Clause 11, wherein the primate is a human.
13. The method according to any of the preceding clauses, wherein the adult mammal is an elderly mammal.
14. The method according to Clause 13, wherein the elderly mammal is a human that is 60 years or older.
15. The method according to any of the preceding clauses, wherein the aging-associated impairment comprises a cognitive impairment.
16. The method according to any of the preceding clauses, wherein the adult mammal suffers from an aging associated disease condition.
17. The method according to any of the preceding clauses, wherein the aging associated disease condition is a cognitive decline disease condition.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of the present invention is embodied by the appended claims.

That which is claimed is:

1. A method of treating an adult mammal for an aging-associated cognitive impairment, the method comprising:
   obtaining blood from an adult mammal;
   extra-corporeally processing the obtained blood to remove β2-microglobulin (B2M) from the obtained blood of the adult mammal to produce B2M depleted blood; and
   returning the B2M depleted blood to the adult mammal in a manner sufficient to treat the adult mammal for the aging-associated cognitive impairment.

2. The method of claim 1, wherein the mammal is a primate.

3. The method according to claim 2, wherein the primate is a human.

4. The method of claim 1, wherein the adult mammal is an elderly mammal.

5. The method according to claim 4, wherein the elderly mammal is a human that is 60 years or older.

* * * * *

SEQUENCE LISTING

```
<160> NUMBER OF SEQ ID NOS: 8

<210> SEQ ID NO 1
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 1
gauucagguu uacucacgut t                                                21

<210> SEQ ID NO 2
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 2
```

```
acgugaguaa accugaauct t                                              21

<210> SEQ ID NO 3
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 3
gccactccca ccctttctca t                                              21

<210> SEQ ID NO 4
<211> LENGTH: 15
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(2)
<223> OTHER INFORMATION: Residue is a locked nucleic acid nucleoside
<220> FEATURE:
<221> NAME/KEY: misc_feature
<222> LOCATION: (14)..(15)
<223> OTHER INFORMATION: Residue is a locked nucleic acid nucleoside
<220> FEATURE:
<221> NAME/KEY: misc_feature
<222> LOCATION: (14)..(15)
<223> OTHER INFORMATION: Residue is 5-methyl cytosine

<400> SEQUENCE: 4
agttgccagc cctnn                                                     15

<210> SEQ ID NO 5
<211> LENGTH: 15
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(2)
<223> OTHER INFORMATION: Residue is a locked nucleic acid nucleoside
<220> FEATURE:
<221> NAME/KEY: misc_feature
<222> LOCATION: (1)..(1)
<223> OTHER INFORMATION: Residue is modified with cis-13-Doco-senol
      (crucyl alcohol)
<220> FEATURE:
<221> NAME/KEY: misc_feature
<222> LOCATION: (1)..(1)
<223> OTHER INFORMATION: Residue is linked to a lipophilic residue with
      a disulfide linker
<220> FEATURE:
<221> NAME/KEY: misc_feature
<222> LOCATION: (14)..(15)
<223> OTHER INFORMATION: Residue is a locked nucleic acid nucleoside
<220> FEATURE:
<221> NAME/KEY: misc_feature
<222> LOCATION: (14)..(15)
<223> OTHER INFORMATION: Residue is 5-methyl cytosine

<400> SEQUENCE: 5
agttgccagc cctnn                                                     15

<210> SEQ ID NO 6
<211> LENGTH: 15
<212> TYPE: DNA
<213> ORGANISM: Artificial sequence
<220> FEATURE:
```

<223> OTHER INFORMATION: Synthetic oligonucleotide
<220> FEATURE:
<221> NAME/KEY: misc_feature
<222> LOCATION: (1)..(2)
<223> OTHER INFORMATION: Residue is a locked nucleic acid nucleoside
<220> FEATURE:
<221> NAME/KEY: misc_feature
<222> LOCATION: (1)..(1)
<223> OTHER INFORMATION: Residue is modified with 1-Tetradeca-nol
    (myristyl alcohol)
<220> FEATURE:
<221> NAME/KEY: misc_feature
<222> LOCATION: (1)..(1)
<223> OTHER INFORMATION: Residue is linked to a lipophilic residue with
    a disulfide linker
<220> FEATURE:
<221> NAME/KEY: misc_feature
<222> LOCATION: (14)..(15)
<223> OTHER INFORMATION: Residue is a locked nucleic acid nucleoside
<220> FEATURE:
<221> NAME/KEY: misc_feature
<222> LOCATION: (14)..(15)
<223> OTHER INFORMATION: Residue is 5-methyl cytosine

<400> SEQUENCE: 6
agttgccagc cctnn                                                        15

<210> SEQ ID NO 7
<211> LENGTH: 15
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(2)
<223> OTHER INFORMATION: Residue is a locked nucleic acid nucleoside
<220> FEATURE:
<221> NAME/KEY: misc_feature
<222> LOCATION: (1)..(1)
<223> OTHER INFORMATION: Residue is modified with Dierucyl-alcohol
<220> FEATURE:
<221> NAME/KEY: misc_feature
<222> LOCATION: (1)..(1)
<223> OTHER INFORMATION: Residue is linked to a lipophilic residue with
    a disulfide linker
<220> FEATURE:
<221> NAME/KEY: misc_feature
<222> LOCATION: (14)..(15)
<223> OTHER INFORMATION: Residue is a locked nucleic acid nucleoside
<220> FEATURE:
<221> NAME/KEY: misc_feature
<222> LOCATION: (14)..(15)
<223> OTHER INFORMATION: Residue is 5-methyl cytosine

<400> SEQUENCE: 7
agttgccagc cctnn                                                        15

<210> SEQ ID NO 8
<211> LENGTH: 15
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(2)
<223> OTHER INFORMATION: Residue is a locked nucleic acid nucleoside
<220> FEATURE:
<221> NAME/KEY: misc_feature
<222> LOCATION: (1)..(1)
<223> OTHER INFORMATION: Residue is linked to a lipophilic residue with
    a disulfide linker
<220> FEATURE:
<221> NAME/KEY: misc_feature

```
<222> LOCATION: (1)..(1)
<223> OTHER INFORMATION: Residue is modified with Erucyl-myristyl-
      glycerol
<220> FEATURE:
<221> NAME/KEY: misc_feature
<222> LOCATION: (14)..(15)
<223> OTHER INFORMATION: Residue is a locked nucleic acid nucleoside
<220> FEATURE:
<221> NAME/KEY: misc_feature
<222> LOCATION: (14)..(15)
<223> OTHER INFORMATION: Residue is 5-methyl cytosine

<400> SEQUENCE: 8
agttgccagc cctnn                                                    15
```